(12) United States Patent
Holmqvist

(10) Patent No.: US 11,707,574 B2
(45) Date of Patent: Jul. 25, 2023

(54) ACTIVATOR FOR A MEDICAMENT DELIVERY DEVICE

(71) Applicant: SHL MEDICAL AG, Zug (CH)

(72) Inventor: Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 442 days.

(21) Appl. No.: 16/954,469

(22) PCT Filed: Dec. 5, 2018

(86) PCT No.: PCT/EP2018/083700
§ 371 (c)(1),
(2) Date: Jun. 16, 2020

(87) PCT Pub. No.: WO2019/121024
PCT Pub. Date: Jun. 27, 2019

(65) Prior Publication Data
US 2021/0077737 A1    Mar. 18, 2021

(30) Foreign Application Priority Data
Dec. 20, 2017   (EP) ...................................... 17208821

(51) Int. Cl.
*A61M 5/315*    (2006.01)
*A61M 5/19*     (2006.01)

(52) U.S. Cl.
CPC .......... *A61M 5/31501* (2013.01); *A61M 5/19* (2013.01); *A61M 5/3159* (2013.01); *A61M 5/31511* (2013.01)

(58) Field of Classification Search
CPC ............... A61M 5/31501; A61M 5/19; A61M 5/31511; A61M 5/3159; A61M 5/2033;
(Continued)

(56) References Cited

U.S. PATENT DOCUMENTS

2013/0317427 A1   11/2013   Brereton et al.
2015/0250953 A1*   9/2015   Elmen .................... A61M 5/19
                                                                       604/91

FOREIGN PATENT DOCUMENTS

CN    103347557 A    10/2013
EP      2438947 A1    4/2012
(Continued)

OTHER PUBLICATIONS

International Search Report and Written Opinion for Int App. No. PCT/EP2018/08370, completed Jan. 7, 2019.

*Primary Examiner* — Katherine H Schwiker
*Assistant Examiner* — Hong-Van N Trinh
(74) *Attorney, Agent, or Firm* — McDonnell Boehnen Hulbert & Berghoff LLP

(57) ABSTRACT

A medicament delivery device is presented that has a manually operable activator element, an activator blocker operably arranged to the activator element, where the activator blocker defines at least one locking member. A medicament delivery device housing is included having at least one flexible hook, wherein the at least one flexible hook of the medicament delivery device housing is operably between a locked position and an unlocked position. In the locked position the flexible hook is releasably engaged with the at least one locking member of the activator blocker, thereby preventing operation of said activator element and in the unlocked position the flexible hook is out of engagement with the at least one locking member of the activator blocker, thereby allowing operation of said activator element.

19 Claims, 26 Drawing Sheets

(58) Field of Classification Search
CPC .. A61M 2005/2073; A61M 2005/2451; A61M 5/2448; A61M 5/284; A61M 5/31571; A61M 5/3158; A61M 5/31596
See application file for complete search history.

(56) References Cited

FOREIGN PATENT DOCUMENTS

| | | |
|---|---|---|
| TW | I436798 B | 5/2014 |
| TW | I478745 B | 4/2015 |
| TW | 201739440 A | 11/2017 |
| WO | 2011/053225 A1 | 5/2011 |
| WO | 2011/123024 A1 | 10/2011 |
| WO | 2011/126439 A1 | 10/2011 |
| WO | 2014/056874 A1 | 4/2014 |
| WO | 2015/028394 A1 | 3/2015 |
| WO | 2016/055295 A1 | 4/2016 |

* cited by examiner

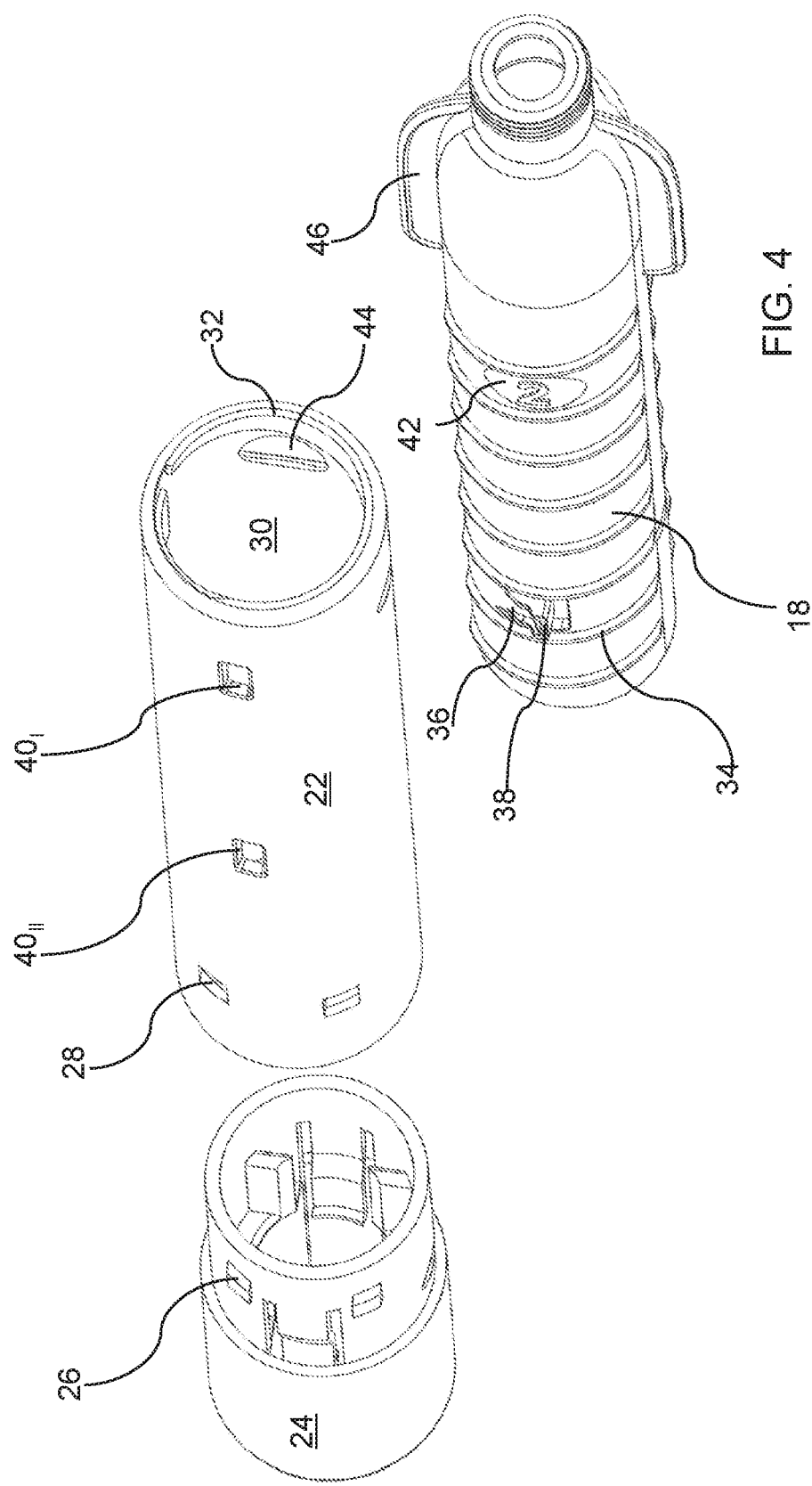

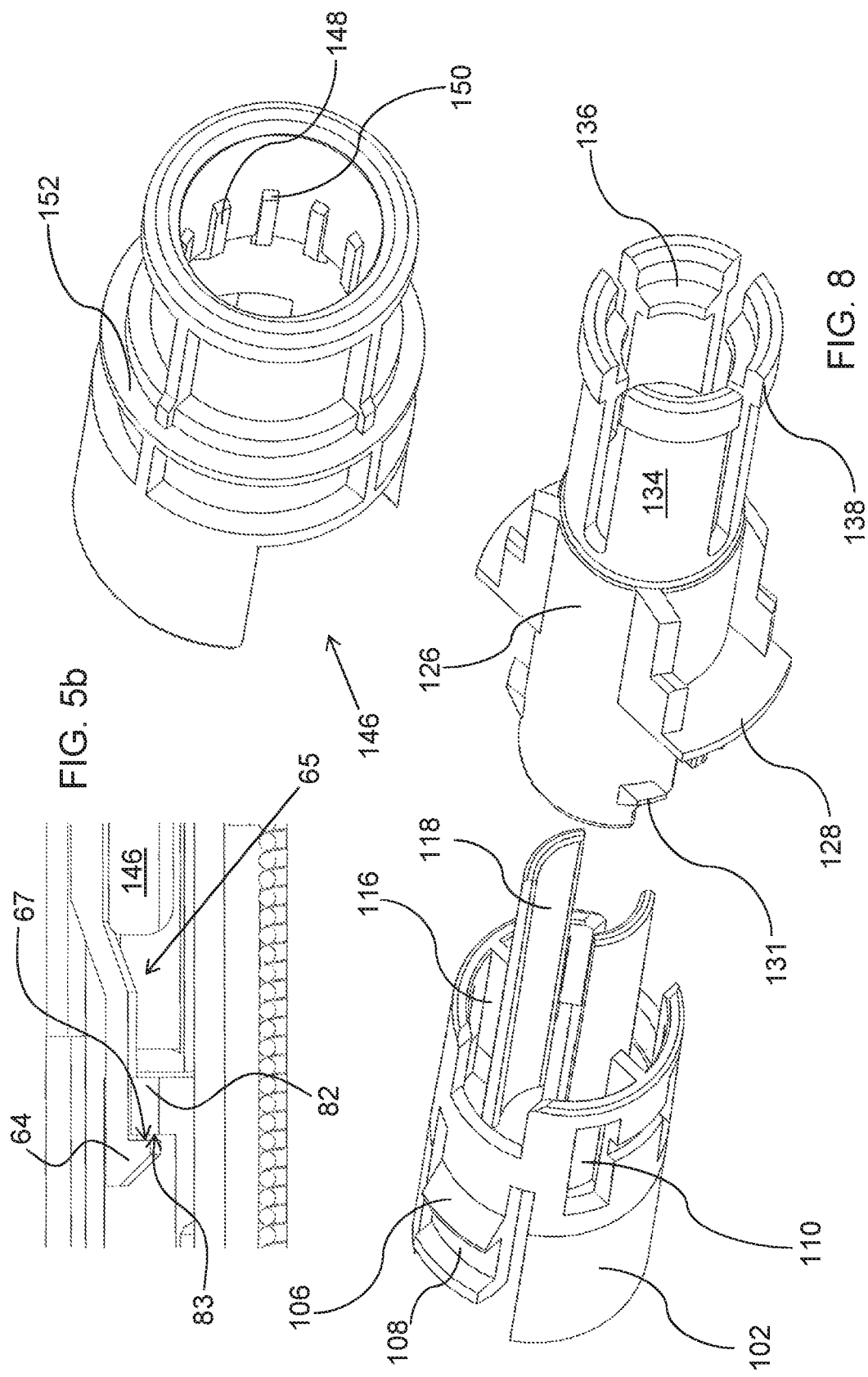

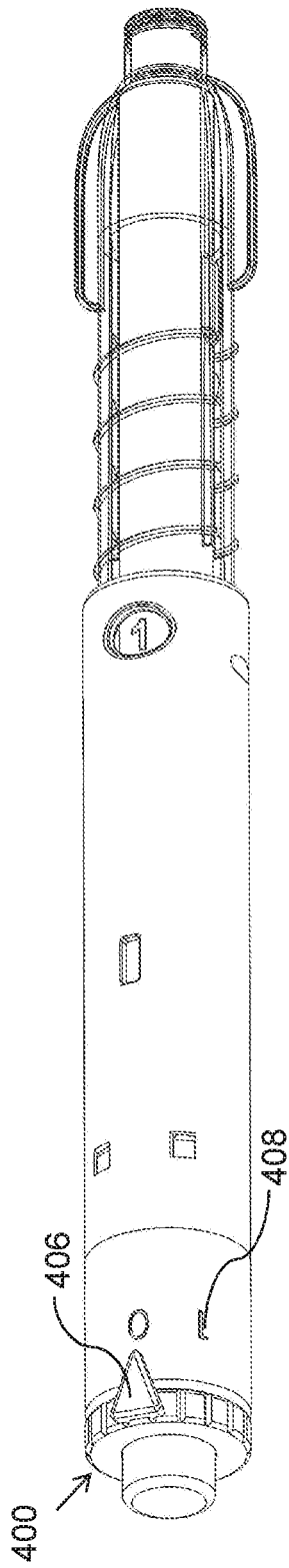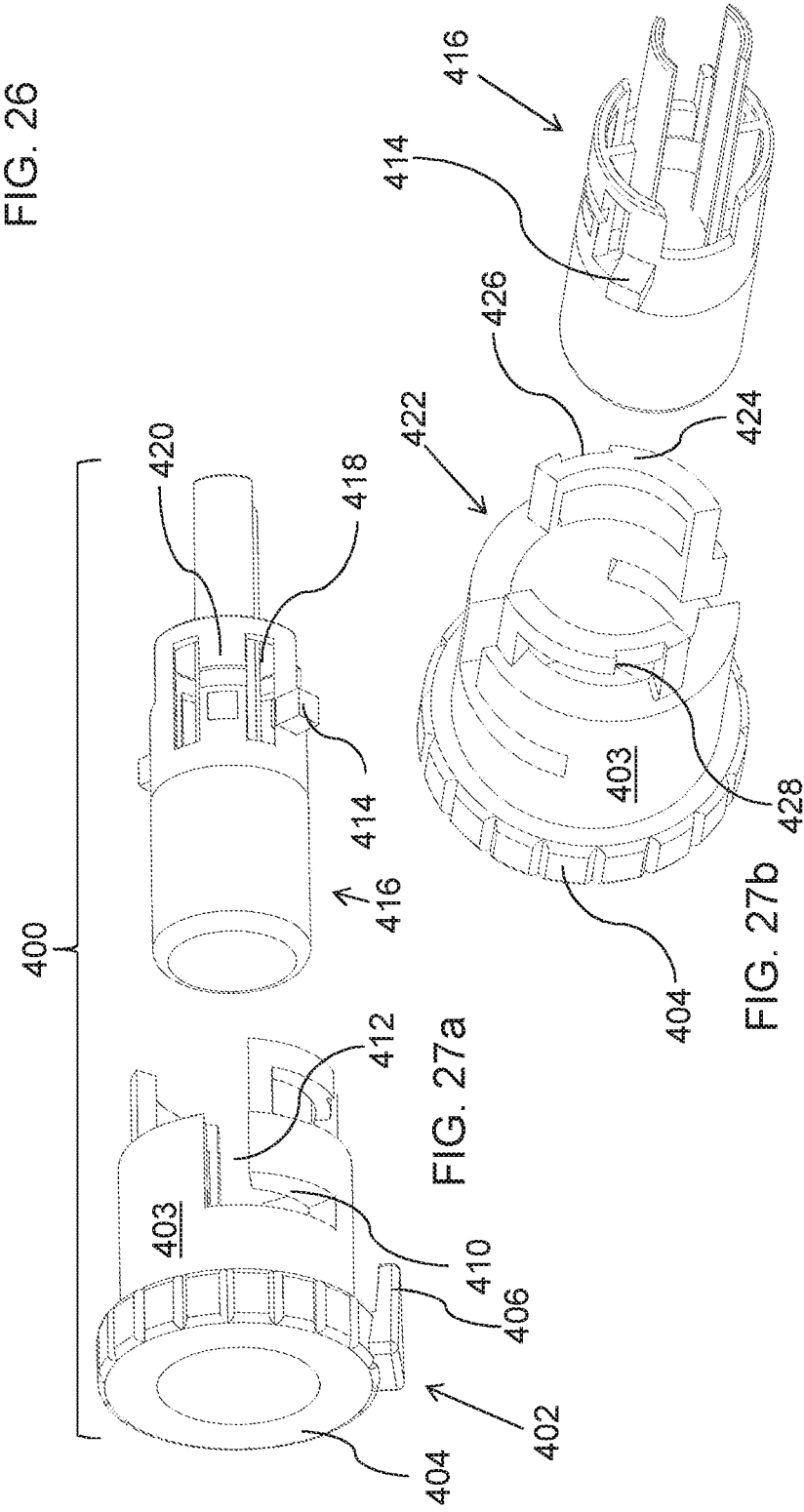

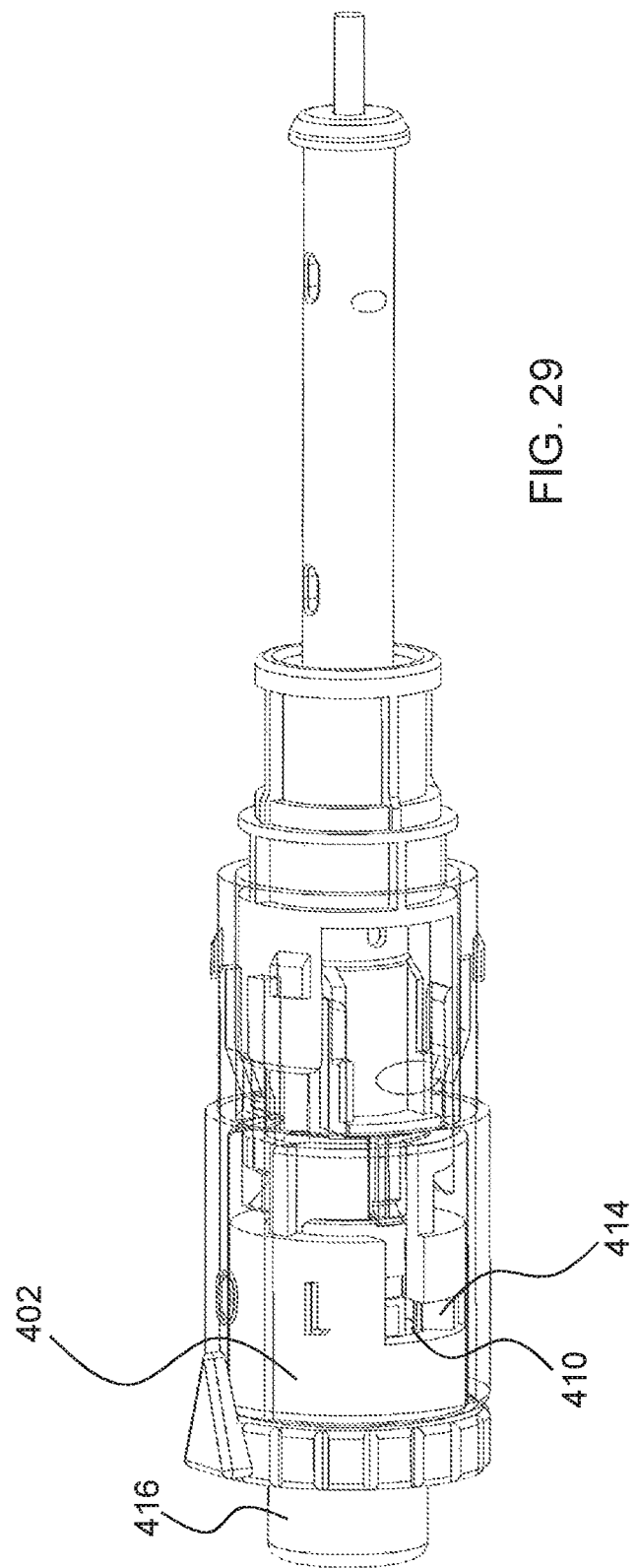

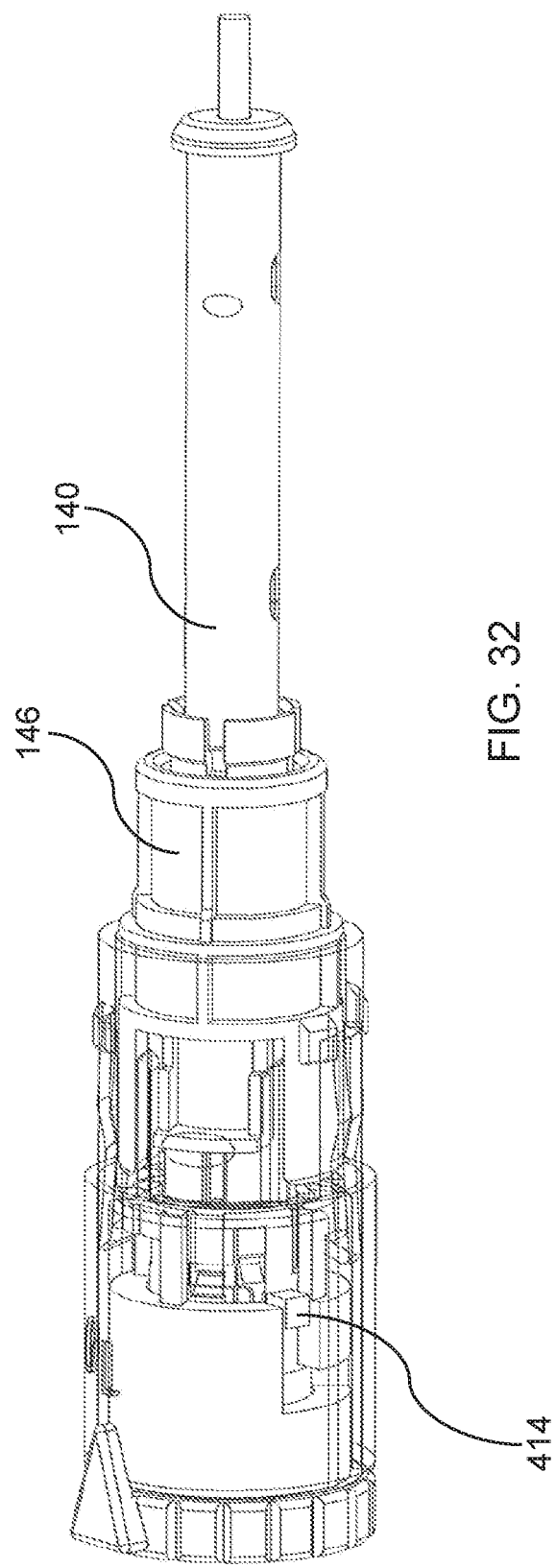

ACTIVATOR FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2018/083700 filed Dec. 5, 2018, which claims priority to European Patent Application No. 17208821.3 filed Dec. 20, 2017. The entire disclosure contents of these applications are herewith incorporated by reference into the present application.

TECHNICAL AREA

The present disclosure relates to an activator for a medicament delivery device and in particular an activator provided with a degree of safety regarding the activation of the medicament delivery device.

BACKGROUND

There are different types of medicaments that can be stored for a long time and that are filled in containers e.g. cartridges, syringes, ampoules, canisters or the like, containing a ready-to-use medicament in liquid state. However, there are also other types of medicaments that are a mixture of two substances, a medicament agent (e.g. lyophilized, powdered or concentrated liquid) and a diluent (e.g. water, dextrox solution or saline solution), wherein these types of medicaments cannot be pre-mixed and stored for a long time because the medicament agent is unstable and can be degraded and loses its effect over a period of time. As such, a user, e.g. a patient himself/herself, a physician, a nurse, hospital personnel or trained persons, has/have to perform the mixing within a certain time period prior to the delivery of a dose of medicament to a patient. Further, some medicament agents are subject to meet chemical changes while mixing. Such sensitive medicament agents require a particular treatment so that, when mixing the medicament agents with a diluent, unreasonable mixing force can degrade the medicament agents.

In order to facilitate the mixing, a number of containers for mixing have been developed comprising at least two chambers, known as multi-chamber containers. These multi-chambered containers comprise a first chamber containing the medicament agent and at least a second chamber containing the diluent. Typically, these chambers may be sealed off with stoppers so that the medicament agents do not become degraded. When the medicament agent is to be mixed shortly before administering, redirecting passages are opened between the chambers, usually by depressing a distal stopper and in turn a divider stopper of the container somewhat.

The above mentioned requirements can be achieved by known medicament delivery devices, such as a common hypodermic syringe, but the procedure is rather awkward, in particular for users not used to handle such devices. In order to facilitate for the patients themselves to administer the medicament with a predetermined dose in an easy, safe and reliable way and also to facilitate the administration of medicaments for hospital personnel in the same facilitated way, an automatic or semi-automatic device is desired having a multiple-chamber solution for obtaining a mixing before delivery.

SUMMARY

The aim of the present application is to provide an improved activator to be used with a medicament delivery device and according to a specific solution a medicament delivery device arranged to handle multi-chamber medicament containers in a safe and reliable way.

The aim is obtained by an activator and a medicament delivery device according to the independent patent claims. Preferable embodiments form the subject of the dependent patent claims.

According to a main aspect, disclosed is an activator for a medicament delivery device, comprising a manually operable activator element. An activator blocker may be operably arranged to the activator element, where the activator blocker may define at least one locking member. A medicament delivery device housing may comprise at least one flexible hook, wherein the at least one flexible hook of the medicament delivery device housing may be operably arranged between a locked position where the flexible hook is releasably engaged with the at least one locking member of the activator blocker, thereby preventing operation of said activator element; and an unlocked position where the flexible hook is out of engagement with the at least one locking member of the activator blocker, thereby allowing operation of the activator element.

Thus a flexible hook that is stationary in a housing of a medicament delivery device may be used for releasably locking an activator blocker such that the activator cannot be operated by a user until the flexible hook is moved out of engagement. This provides a robust solution with few components yet providing an enhanced security of the handling of a medicament delivery device provided with the activator.

According to one feasible solution, the flexible hook may be provided with engagement surfaces arranged to engage with stop surfaces of the activator blocker when in the locked position.

In that regard, the engagement surfaces of said hook may be directed in a proximal direction and wherein the stop surfaces of the movable activator element may be directed in a distal direction, preventing movement of the activator blocker in a distal direction in the locked position. Thus, when the activator is to be moved in a distal direction in order to release the activator, this solution is applicable.

One example is when the activator blocker may comprise a blocking element that may enclose the activator element and that the activator blocker and the activator may comprise engagement elements. The activator blocker may be movable in a distal direction in relation to the activator when in the unlocked position such that the engagement elements engage the activator blocker with the activator, enabling a manual movement in the proximal direction of the activator blocker and the activator.

In more detail, the engagement elements may comprise flexible tongues on the activator having ledges that are intended to engage with ledges of the activator blocker.

Another example is when the activator blocker may comprise a blocking element enclosing the activator element and that activator blocker may be movable in the distal direction in the unlocked position. Here the activator blocker is removed and the activator is exposed, enabling movement of the activator in the proximal direction.

As an alternative, the engagement surfaces of the hook may be directed in a distal direction and wherein the stop surfaces of the movable activator element are directed in a proximal direction, preventing movement of the activator blocker in a proximal direction in the locked position.

With this solution, the activator blocker may comprise a blocking element enclosing the activator element, wherein the activator blocker may be movable in the proximal direction in the unlocked position, also enabling movement of the activator in the proximal direction.

In a further alternative, the activator blocker may comprise a generally tubular member arranged turnable in relation to the housing between the initial position and the activated position. The activator may be arranged coaxial inside the activator blocker and protruding in the distal direction, that the activator blocker and the activator may be provided with engagement elements that in the locked position engage such to prevent movement of the activator in the proximal direction and in the unlocked position are moved out of engagement, allowing movement of the activator in the proximal direction.

In more detail, the engagement elements of the activator may comprise protrusions, and the engagement elements of the activator blocker may comprise a first transversally extending groove and a proximally extending groove.

According to a further aspect, the flexible hooks may be arranged to engage with a locking structure of the activator element for locking the activator element after manual operation. In this manner it is ensured that the activator element cannot be operated further, and also provides an indication to a user that the medicament delivery device is used and should be discarded.

According to a further main aspect of the application, a medicament delivery device is provided having a housing comprising a proximal housing part and a distal housing part, where the proximal housing part may be arranged to accommodate a multi chamber medicament container. The housing parts are preferably arranged movable in relation to each other from an initial position to a mixed position in which the content of the multi chamber medicament container is mixed. Further the medicament delivery device may comprise a drive unit arranged to act on the multi chamber medicament container for expelling a dose of medicament. Moreover, the medicament delivery device is provided with an activator operably connected to the drive unit and arranged with a manually operable activator element wherein the activator is manually operable in a proximal direction between an inactive position and an active position in which the drive unit is activated.

In line with previous aspects of the application, an activator blocker may be operably arranged to the activator element, where the activator blocker defines at least one locking member and the distal housing part comprising at least one flexible hook, wherein the at least one flexible hook of the distal housing part is operably arranged between a locked position where the flexible hook is releasably engaged with the at least one locking member of the activator blocker, thereby preventing operation of said activator element; and an unlocked position where the flexible hook is out of engagement with the at least one locking member of the activator blocker, thereby allowing operation of said activator element, wherein in the mixed position the proximal housing part acts on the flexible hook to move it to the unlocked position.

With this solution it is not possible to operate the activator until the multi chamber medicament container of the medicament delivery device has been mixed by moving the two housing parts together. Until the mixing is completed, the drive unit cannot be activated in any way, increasing the safety of the medicament delivery device.

Regarding the aspect of the drive unit, the medicament delivery device may further comprise an actuator sleeve operably connected to the proximal housing part so as to move in conjunction with the proximal housing part and to act on the flexible hook, which actuator sleeve cooperates with an actuator of the drive unit for holding a plunger rod in an energized state.

Moreover, the actuator may be generally tubular, accommodating the plunger rod, wherein the actuator may comprise arms that are flexible in a generally transversal direction, that the free ends of the arms are arranged with radially inwardly directed ledges that fit into recesses of the plunger rod. Also, the activator may be arranged with proximally directed fingers extending into the actuator and being in contact with a distal end of the plunger rod.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 4 is a detailed view of components of a first embodiment of an activator of the medicament delivery device of FIG. 1, FIG. 8 is a detailed view of components of a first embodiment of an activator of the medicament delivery device of FIG. 1, FIG. 26 is a side view of a medicament delivery device comprising a fourth embodiment of an activator;

FIG. 27a is a detailed view of components of the fourth embodiment of an activator of the medicament delivery device of FIG. 26, FIG. 27b is a detailed views of components of the fourth embodiment of an activator of the medicament delivery device of FIG. 26.

FIG. 29 is a side view of the medicament delivery device of FIG. 26 with certain components removed for clarity, displaying different functional stages.

FIG. 32 is a side view of the medicament delivery device of FIG. 26 with certain components removed for clarity, displaying different functional stages.

DETAILED DESCRIPTION

Figure 1:
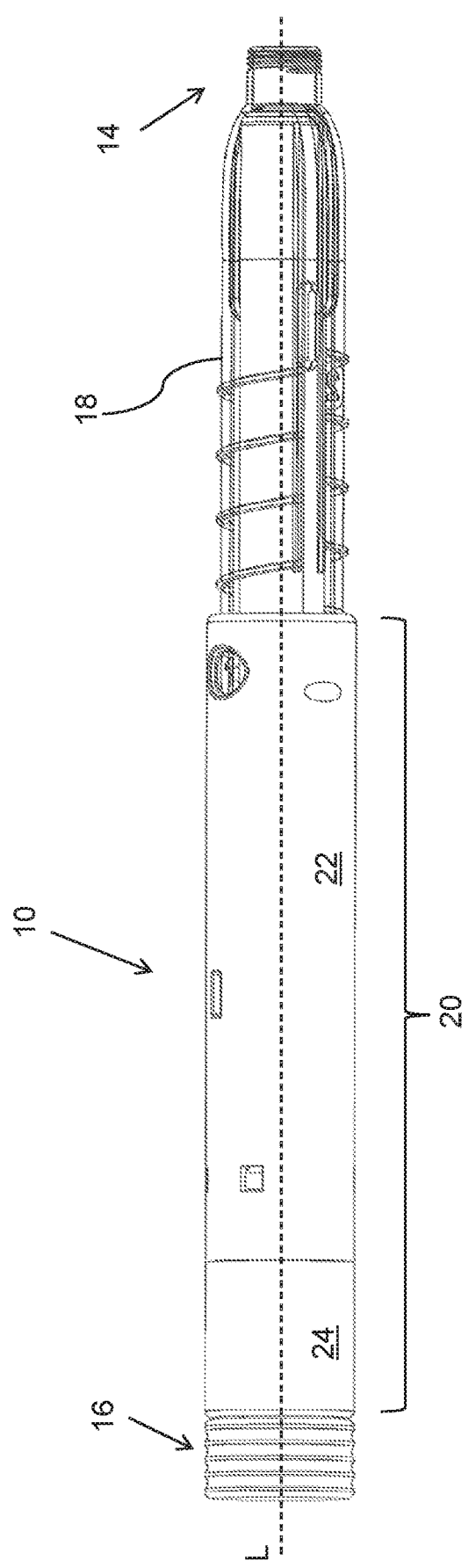
FIG. 1 is a side view of a medicament delivery device that may comprise an activator according to one aspect of the application.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

An aim of the present disclosure is to provide an improved medicament delivery device capable of handling medicament delivery wherein the risk of accidental premature firing of the device is precluded or minimized. In the present disclosure, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

FIG. 1 illustrates a side view of an exemplary drug delivery device 10. As illustrated, the medicament delivery device 10 comprises a housing that extends from a proximal end 14 to a distal end 16. More preferably, the medicament delivery device 10 comprises a generally elongated housing extending along a longitudinal axis L of the medicament delivery device, which housing comprises a proximal housing part 18 and a distal housing part 20. In one preferred arrangement, the proximal housing part 18 and the distal housing part 20 are arranged and mounted to be movable relative each other along the longitudinal axis L of the medicament delivery device 10. In one preferred arrangement, the distal housing part 20 comprises two housing component parts: a front distal housing part 22 and a rear distal housing part 24. The front distal housing part 22 and the rear distal housing part 24 may be permanently or non-permanently coupled to one another. In the embodiment shown, FIG. 4, the rear distal housing part 24 is arranged with outwardly directed protrusions 26 that are arranged to fit into recesses 28 in the front distal housing part 22, creating a lock between the housing parts. The proximal end of the front distal housing part 22 is arranged with a central passage 30 through which the proximal housing part may extend. The inner edge surface of the passage 30 is arranged with thread segments 32 that are arranged and intended to cooperate with corresponding thread segments 34 or threads on an outer surface of the proximal housing part 18 as seen in FIG. 4.

Moreover, the proximal housing part 18 is arranged with a generally circumferentially extending arm 36 being flexible in the generally radial direction. The free end of the arm 36 is arranged with an outwardly extending ledge 38. The ledge 38 is arranged to fit into two cut-outs 40, on the front distal housing part, one 401 near the proximal end and one 4011 approximately midway along the housing 22, the function of which will be explained below. The outer surface of the proximal housing part is further arranged with two insignia 42, such as numeral 1 and 2, which insignia are designed to be visible in a window 44 in the front distal housing part 22 as will be described. Moreover, the proximal housing part 18 is arranged with plate- or wing-shaped protrusions 46 at a proximal area thereof, providing a grip for a user as will be explained. Further, the proximal end of the proximal housing part 18 is arranged with a neck portion 48, onto which a medicament delivery member (not shown) is arranged to be attached, either permanently or removably. In the embodiment shown, the neck portion 48 is provided with outer threads that are arranged to cooperate with corresponding threads on a medicament delivery member. It is of course possible to utilize other types of fastening elements such as bayonet couplings or luer connections.

Figure 2:
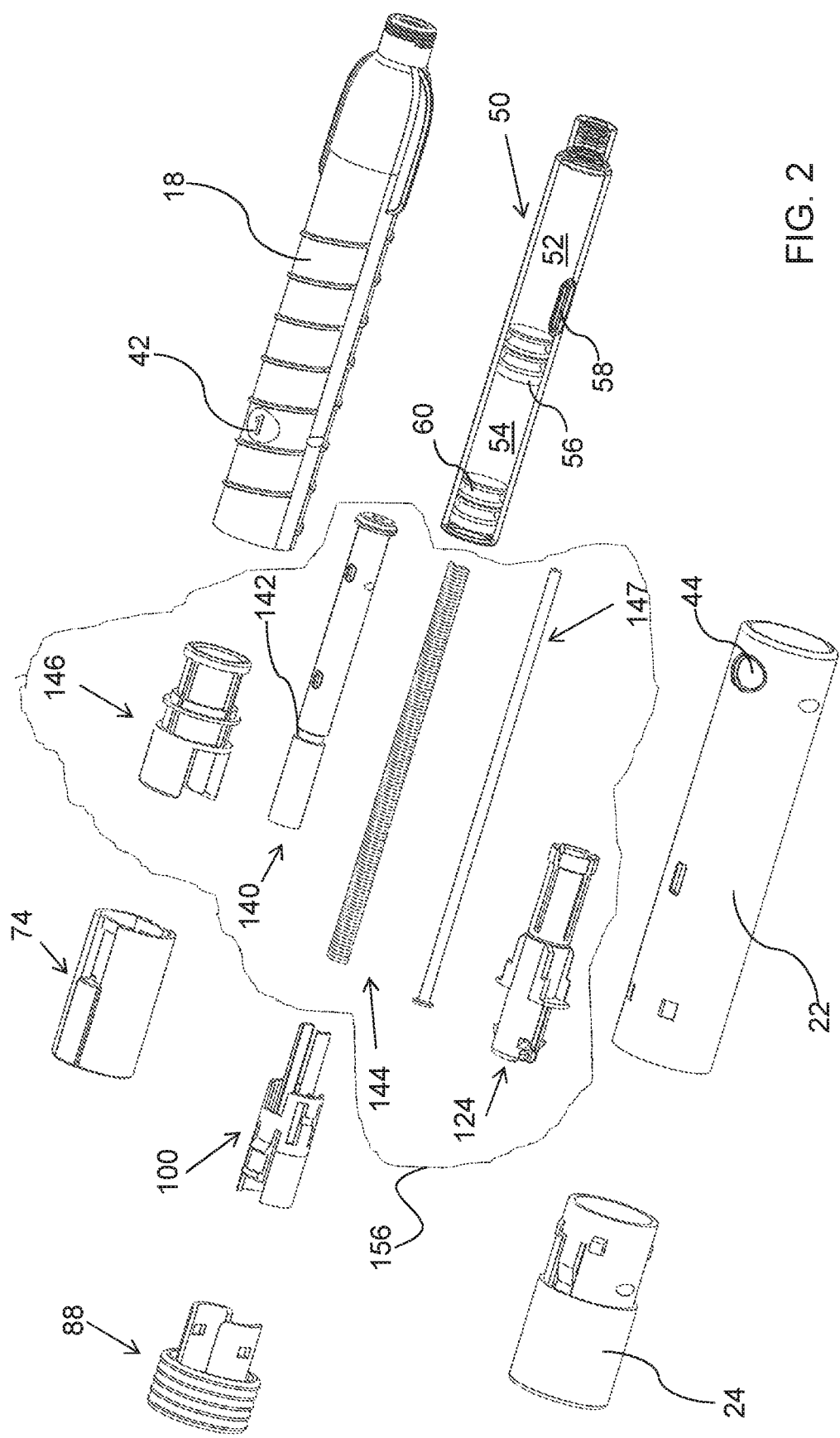
FIG. 2 is an exploded view of the medicament delivery device according to FIG. 1.

The proximal housing part 18 is arranged to accommodate a multi-chamber medicament container 50 and as disclosed herein, comprises e.g. a dual chamber container designed with a first compartment 52 and a second compartment 54, FIG. 2. In one arrangement, one compartment of the two compartments contains preferably the medicament in powder form and the other compartment contains preferably a diluent. The two compartments are separated by a resilient, movable stopper 56 (i.e., a proximal stopper), which stopper when moved, opens passages 58 between the compartments for mixing the medicament with the diluent. A distally arranged second stopper 60 (i.e., a distal stopper) closes a distal end of the medicament container 50.

Figure 5A:
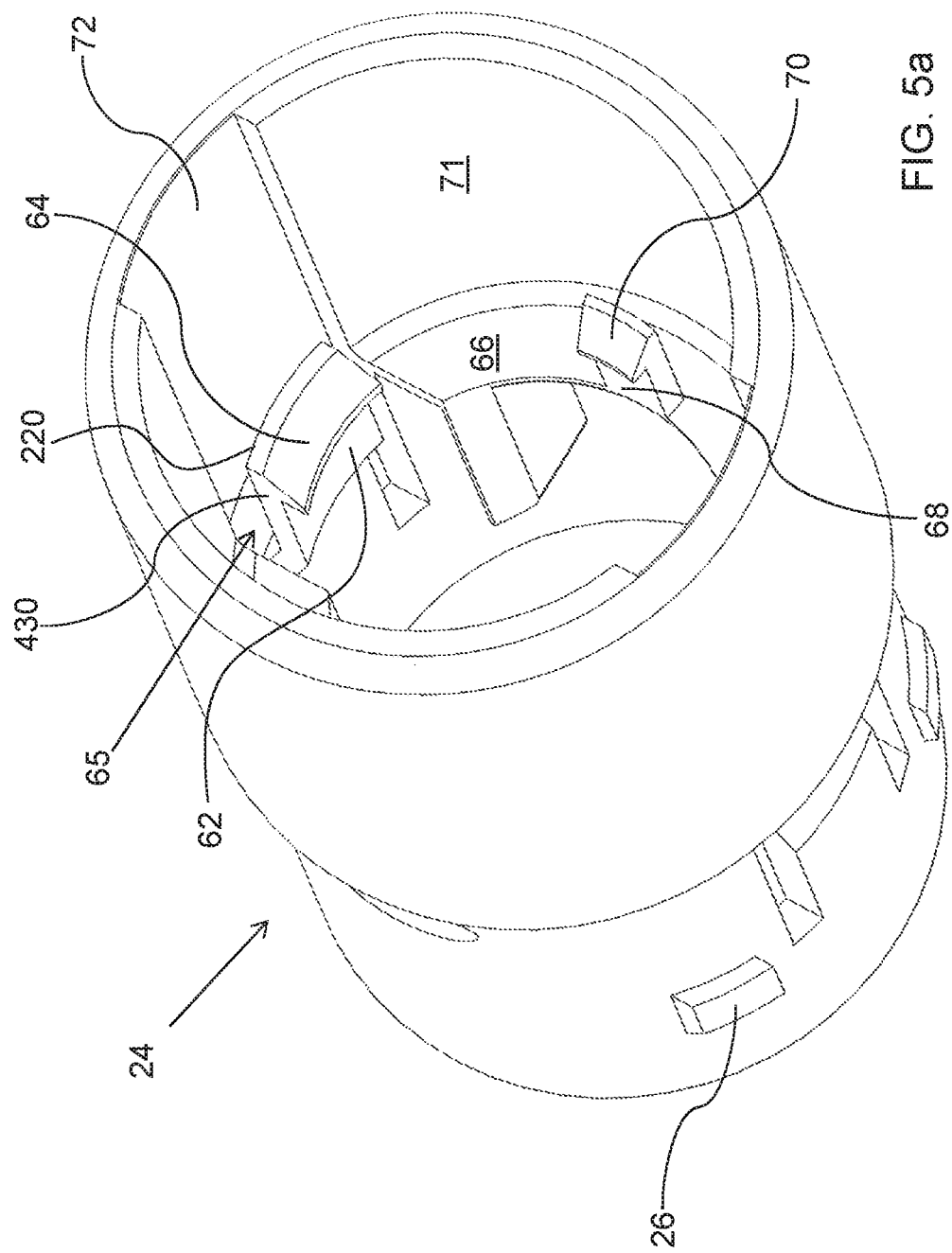
FIG. 5 is a detailed view of components of a first embodiment of an activator of the medicament delivery device of FIG. 1.

As illustrated in FIG. 5*a*, the rear distal housing part 24 comprises one or more generally radially flexible tongues 62 provided along an interior wall surface of a tubular proximal area, which tongues 62 are extending in the distal direction. The free ends of the tongues 62 are provided with generally wedge-shaped inwardly directed ledges 64, where the tongues 62 and the ledges 64 form hooks 65 that are flexible in the generally radial direction. The ledges 64 of the hooks 65 are arranged with proximally directed engagement surfaces 67 as seen in FIG. 5*b*. The rear distal housing part 24 is further arranged with a transversal wall section 66 having a distally directed surface and a proximally directed surface. The distally directed surface is provided with distally directed protrusions 68, which protrusions are arranged with wedge-shaped inwardly directed ledges 70. The inner surface of a tubular distal area 71 of the rear distal housing part 24 is moreover arranged with longitudinally extending grooves 72, which grooves are aligned in the longitudinal direction with the flexible tongues 62, wherein the tongues 62 are positioned radially inwardly of the grooves 72 as seen in FIG. 5. The tubular distal area 71 is arranged to accommodate a generally tubular activator sleeve 74, FIG. 6, wherein the activator sleeve 74 is provided with generally longitudinally extending ledges 76 on its outer surface at a distal end thereof. The ledges 76 are configured to fit into the grooves 72 of the rear distal housing part 24, causing a rotational lock between the components while allowing relative movement in the longitudinal direction.

Further, generally rectangular cut-outs 78 are arranged proximal of and in line with the ledges 76. At the distal end of the cut-outs 78, generally rectangular, transversally extending and inwardly directed ledges 80 are arranged, forming connection elements. At the proximal end of the cut-outs 78 locking members in the form of generally transversal beams 82 are provided. The beams are arranged with distally directed stop surfaces 83, FIG. 5*b*, arranged to interact with the engagement surfaces 67 of the ledges 64 of the hooks 65 as will be described. At the inner surface of the activator sleeve 74 a number of longitudinally extending ledges 84 are arranged. These ledges 84 are arranged to cooperate with side surfaces of generally arc-shaped arms 86 on an activator blocker 88 of an activator 90, causing a rotational fixation between the activator blocker 88 and the activator sleeve 74. Further the arc-shaped arms 86 are provided with cut-outs 91, which cut-outs 91 are arranged to interact with inwardly directed protrusions 92 on the activator sleeve 74, thereby locking the two components to each other. The distal end of the activator blocker 88 is provided with a generally tubular part 94 having grip elements 96 that in the embodiment shown are circumferentially extending grooves and protrusions. Further an end wall 98 is arranged at the distal end of the activator blocker 88.

Figure 6:
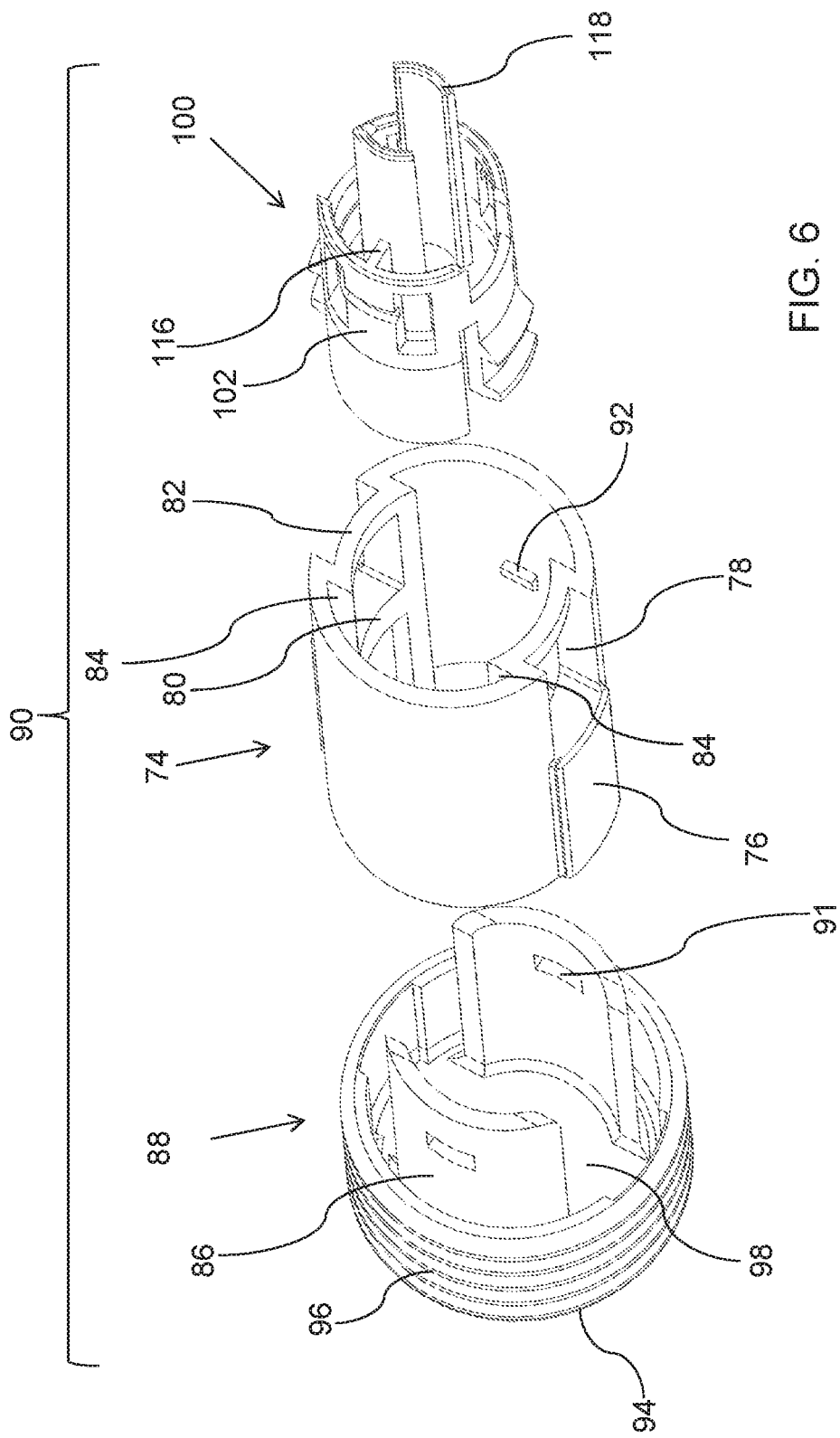
FIG. 6 is a detailed view of components of a first embodiment of an activator of the medicament delivery device of FIG. 1.
Figure 7:
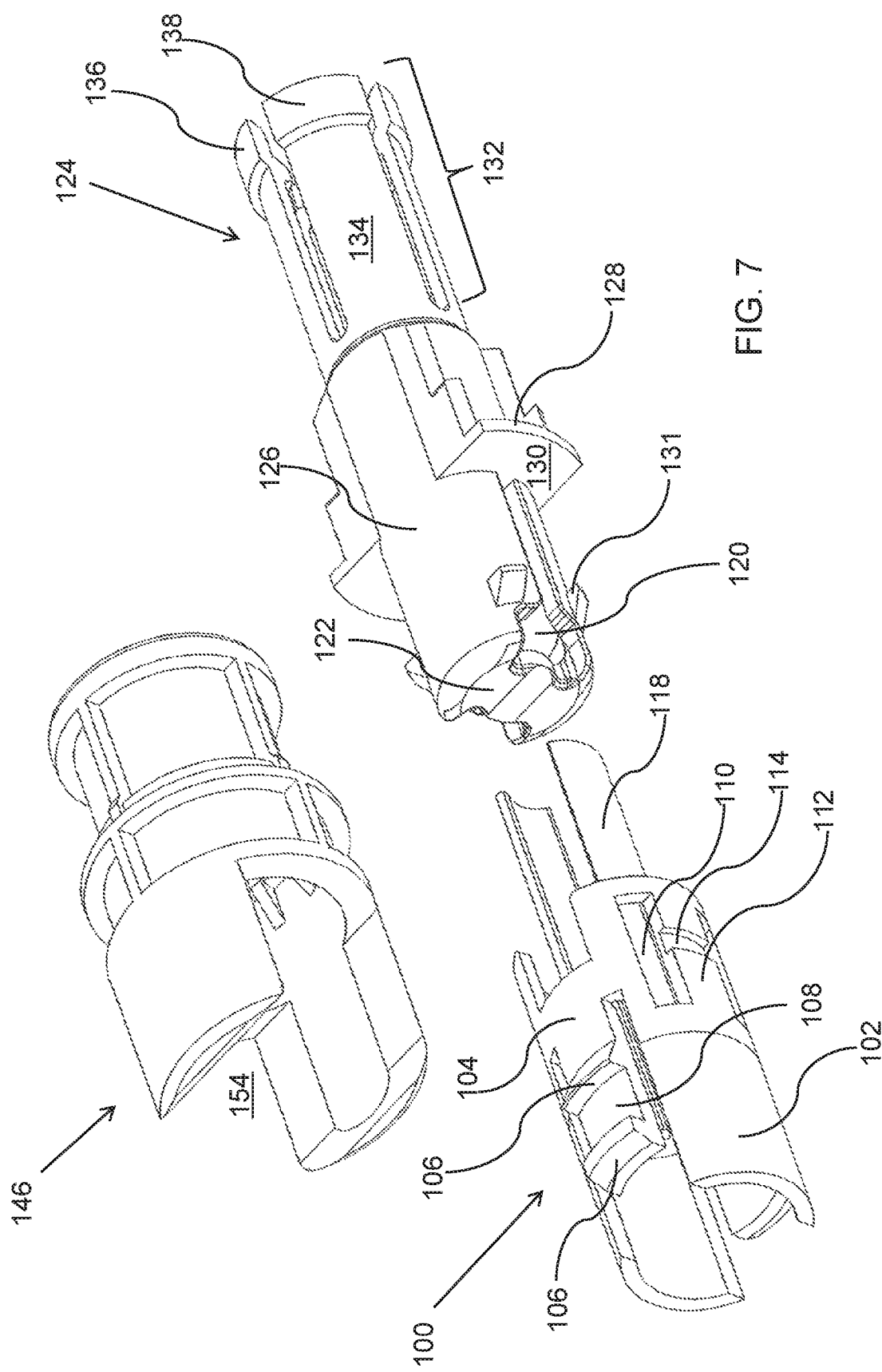
FIG. 7 is a detailed view of components of a first embodiment of an activator of the medicament delivery device of FIG. 1.

An activator element 100, comprised in the activator 90, is arranged coaxial with and inside the activator sleeve 74, FIGS. 6 and 7. The activator element 100 has a distal generally tubular body 102. The tubular body 102 is provided with distally directed arms 104, which arms 104 are flexible in the generally radial direction. The outer surfaces of the arms 104 are provided with two transversal and generally parallel ledges 106 forming a transversal groove 108 between them, which transversal groove 108 is to cooperate with the transversal ledge 80 of the activator sleeve 74 as will be described. The most proximal ledge 106 has a wedge-shape, the function of which will be described below. Further, the side surface of the tubular body 102 is provided with two generally rectangular cut-outs 110, forming a longitudinally extending bridge 112 there between. On the outer side of the bridge 112, a locking structure in the form of a transversally extending groove 114 is arranged, which groove 114 is intended to cooperate with the wedge-shaped ledges 70 of the protrusions 68 of the distal housing part as will be described.

The activator element 102 is further arranged with longitudinally extending, elongated and inwardly directed, ledges 116 placed on inner surfaces of the bridges 112 as seen in FIG. 6. Two proximally directed, generally arc-shaped, elongated fingers 118 are attached to or made integral with the elongated ledges 116. These fingers 118 are designed to fit into generally arc-shaped passages 120 in a distal end wall 122 of an actuator 124, FIG. 7. The actuator 124 is arranged with a distal generally tubular part 126 into which the fingers 118 extend. The tubular part 126 is arranged with oppositely positioned outwardly extending ledges 128, which ledges 128 are provided with distally directed support surfaces 130. On the outer surface of the tubular part 126, a number of outwardly directed protrusions 131 are arranged, which protrusions 131 are intended to fit into the rectangular cut-outs 110 of the activator element 102, creating a rotational lock between the components but allowing relative movement in the longitudinal direction.

The actuator 124 is further arranged with a proximal part 132 which is provided with a number of proximally extending arms 134, in the embodiment shown four arms having free ends that are flexible in the generally radial direction. As illustrated in FIG. 6, each proximally extending arm 134 has both an inwardly directed ledge 136 as well as an outwardly directed ledge 138.

An elongated plunger rod 140 is further arranged coaxial with and inside the actuator 124. The plunger rod 140 is provided with a circumferential groove 142, FIG. 2, in which the inwardly directed ledges 136 of the arms 134 of the actuator 124 may fit. The plunger rod 140 is hollow an inside the plunger rod 140 a drive spring 144 is arranged between a proximal end wall 145 of the plunger rod 140, FIG. 3, and the end wall 122 of the actuator. A guide rod 147 is further arranged inside the drive spring 144 for preventing buckling of the drive spring 144. The proximal end of the plunger rod 140 is designed to act on the distal stopper 60 of the medicament container 50 as will be described.

Outside of and coaxial with the actuator 124 is a generally tubular actuator sleeve 146, FIGS. 7 and 8. The proximal area of the actuator sleeve 146 has a diameter generally corresponding to the outer diameter defined by the outwardly directed ledges 138 of the actuator 124 when the inwardly directed ledges 136 are positioned in the circumferential groove 142 of the plunger rod 140, thereby providing a locking function of the plunger rod 140 as will be described. Further the inner surface of the proximal area is arranged with inwardly directed ledges 148 that form proximal blocking surfaces 150 for distally directed surfaces of the outwardly ledges 138 of the actuator 124, preventing movement of the actuator 124 in the distal direction when the inwardly directed ledges 136 of the actuator are positioned in the groove 142 of the plunger rod 140. The actuator sleeve 146 is further arranged with a proximally directed circumferential ledge 152, FIG. 8, which is to cooperate with a distally directed circumferential surface of the proximal housing part 18 as will be described. Moreover, the distal area of the actuator sleeve is arranged with cut-outs 154, FIG. 7, intended to accommodate the ledges 128 of the actuator 124. The combination of the actuator 124, the plunger rod 140, the drive spring 144, the guide rod 147 and the actuator sleeve 146 forms a drive unit 156 of the medicament delivery device, FIG. 2.

Figure 3:
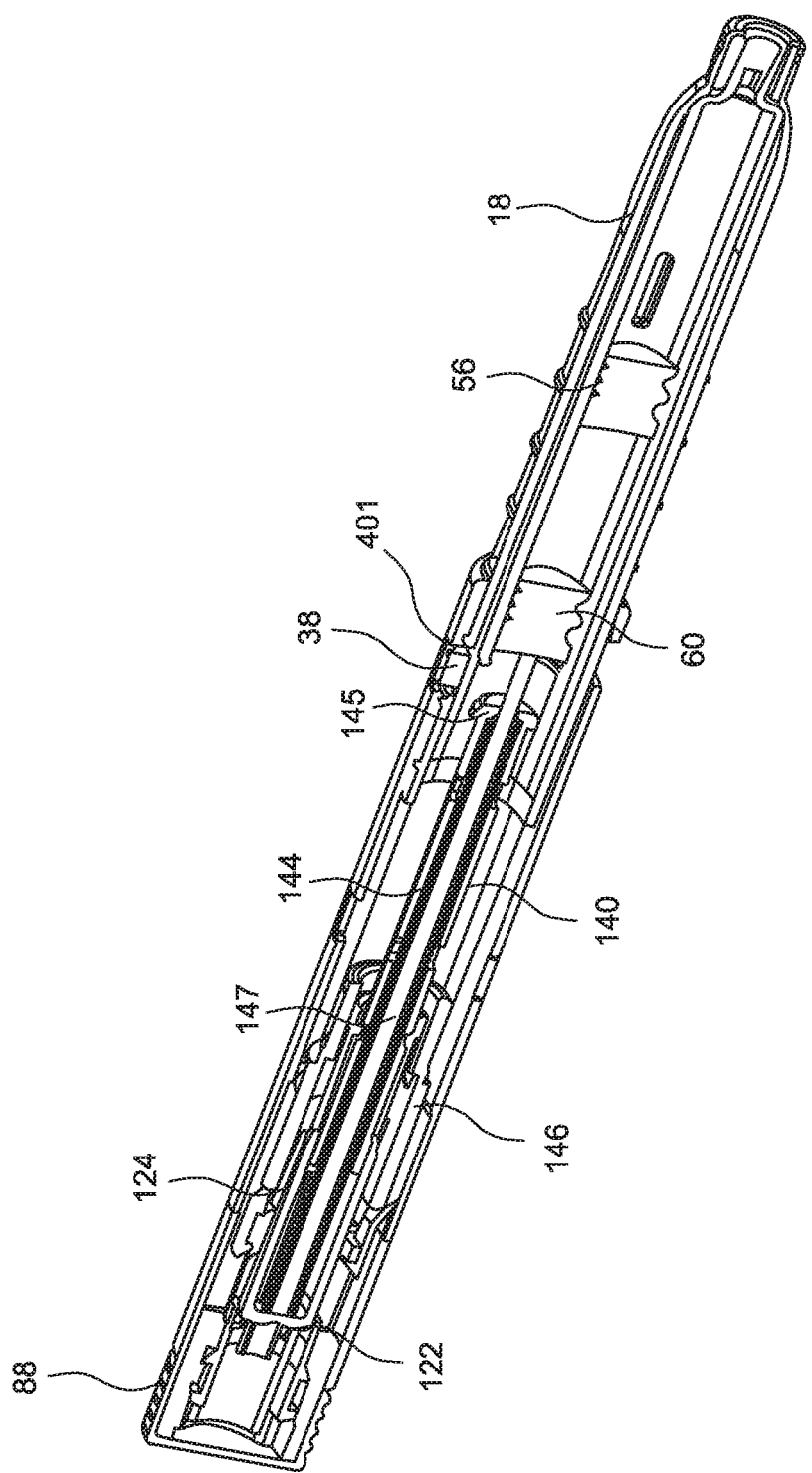
FIG. 3 is a cross-sectional view of the medicament delivery device of FIG. 1.
Figure 9A:
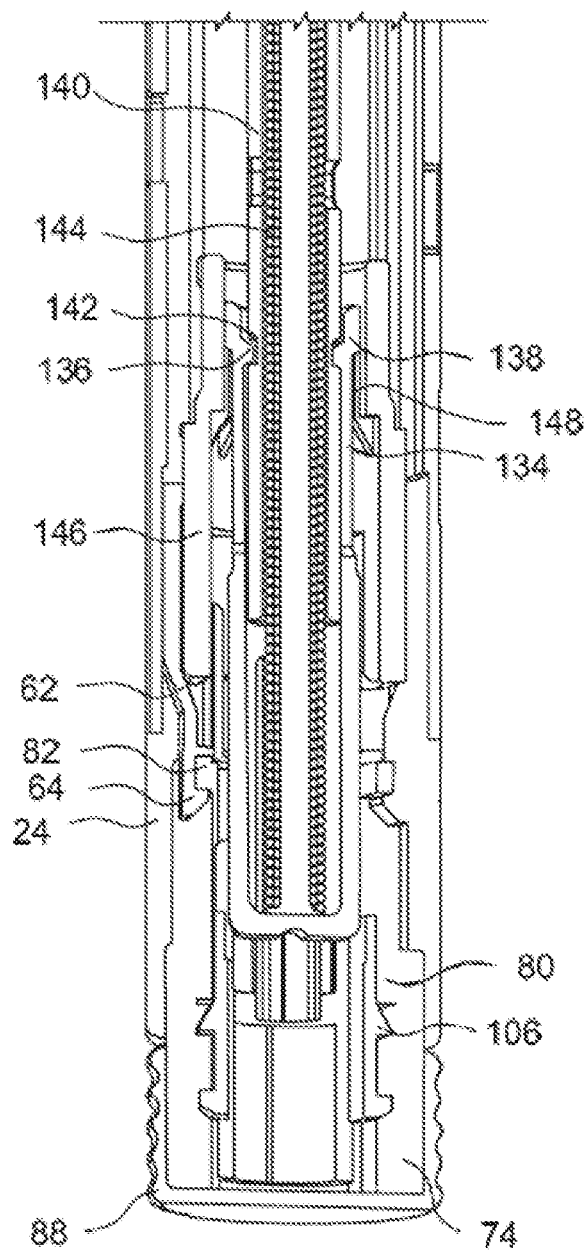
FIG. 9 is a cross-sectional view of different functional stages of the first activator embodiment comprised in a medicament delivery device of FIG. 1.

The device is intended to function as follows. When the device is delivered to a user, a multi-chamber medicament container 50 is positioned in the proximal housing part 18. Further, the proximal housing part 18 is in an extended position in relation to the distal housing part as seen in FIGS. 1 and 3. The drive spring 144 is in a tensioned state inside the plunger rod 140 with the inwardly directed ledges 136 of the actuator 124 positioned in the circumferential groove 142 of the plunger rod 140 as seen in FIG. 9a. The inwardly directed ledges 136 are prevented from leaving the groove 142 due to the actuator sleeve 146 positioned radially outside the arms 134 of the actuator 124 whereby the outwardly directed ledges 138 of the arms 134 of the actuator 124 are in contact with the inner surface of the actuator sleeve 146, FIG. 9a. The actuator sleeve 146 is locked in the longitudinal direction in that its distal end surface is in contact with an inclined part of the tongues 62, and in that the surfaces 150 of the ledges 148 of the actuator sleeve are in contact with distally directed surfaces of the outwardly directed ledges 138 of the actuator 124, FIG. 9a.

Figure 9B:
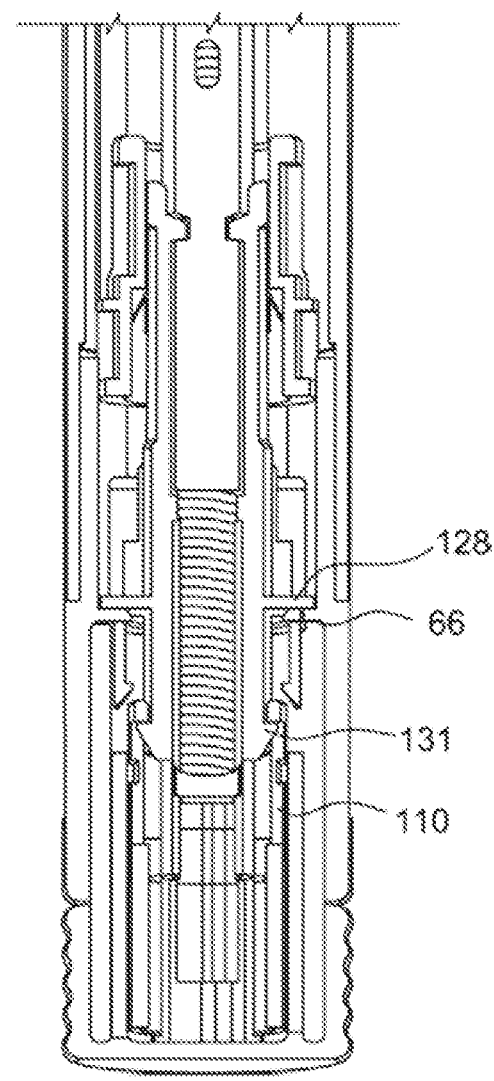

The activator sleeve 74 with the activator blocker 88 is in an initial position where a proximal edge of the activator blocker 88 is in contact with a distal end surface of the distal housing part 24, FIG. 9a. The activator sleeve 74 is further locked in this position in that the engagement surfaces 67 of the ledges 64 of the distally directed tongues 62 of the rear distal housing part 24 engage the stop surfaces 83 of the beams 82 of the activator sleeve 74 as seen in FIG. 9a, thereby preventing any pulling of the activator blocker 88 in the distal direction. Further, the activator element 100 is held in position longitudinally in that the ledge 106 is in contact with the transversal ledge 80 of the activator sleeve 74, preventing movement in the proximal direction of the activator, and in that the protrusions 131 engages the proximal edge of the cut-outs 110, as seen in FIG. 9b, preventing movement in the distal direction of the activator element 100. Further, the actuator 124 with its tensioned plunger rod 140 is also locked in the longitudinal direction by the protrusions 131 as described and also the ledges 128 abutting the transversal wall section 66, FIG. 9b. The ledge 38 of the arm 36 of the proximal housing part 18 is positioned in the first cut-out 401 in the distal housing part, FIG. 3.

When the medicament delivery device is to be used, a user turns the proximal housing part 18 in relation to the distal housing part, preferably with the aid of the grip enhancing protrusions 46, whereby the proximal housing part 18 is moved distally in relation to the distal housing part. The design of the arm 36 and its ledge 38 enables only rotation in the correct direction. The relative movement of the housing parts will cause the plunger rod 140 to move the distal stopper 60 in the proximal direction which in turn will cause a movement of the proximal stopper 56 such that the by-pass passage 58 is opened between the compartments 52 and 54, wherein the diluent may be mixed with the medicament in powder form.

Figures 10, 11:
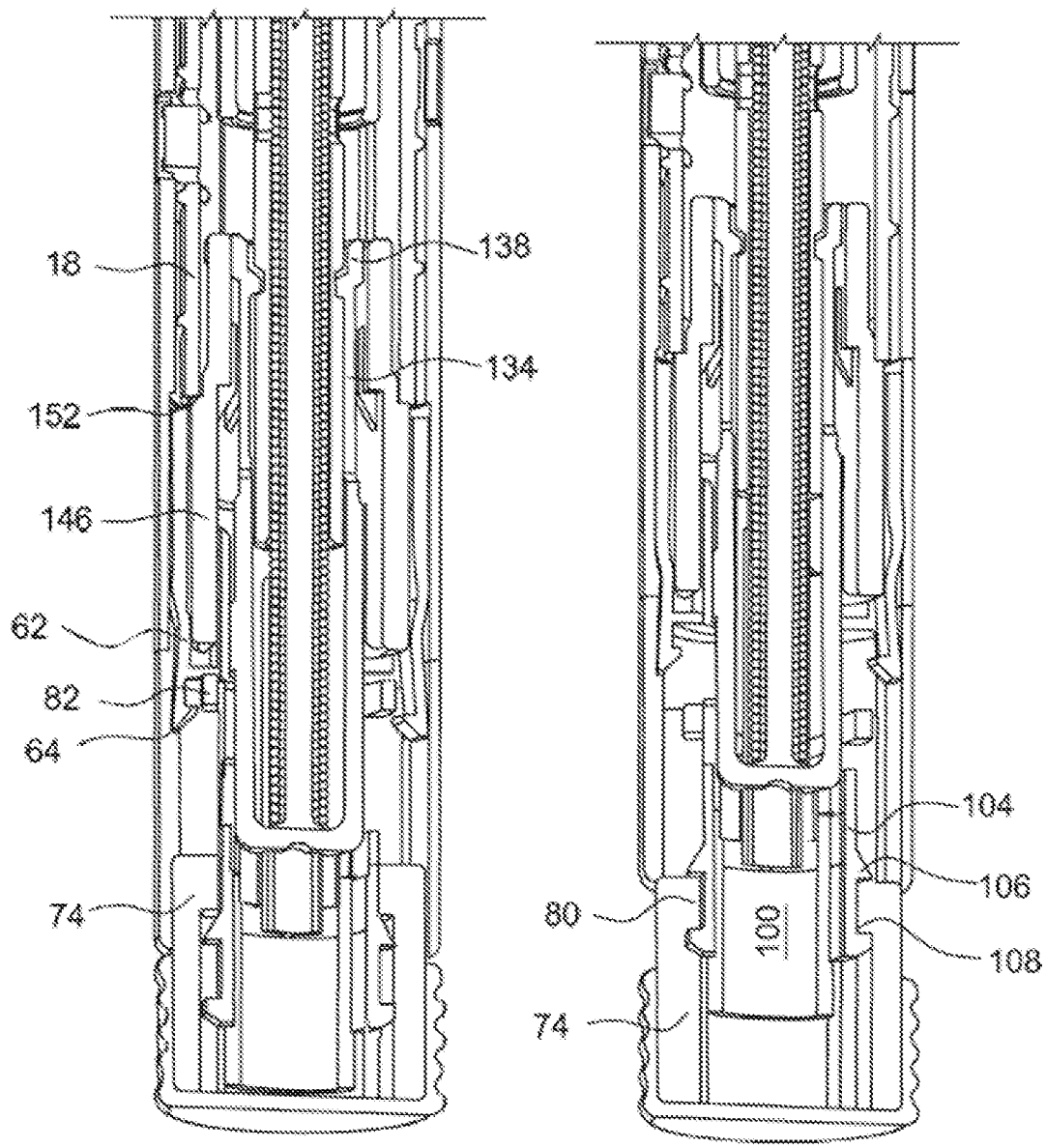
FIG. 10 is a cross-sectional view of different functional stages of the first activator embodiment comprised in a medicament delivery device of FIG. 1.
FIG. 11 is a cross-sectional view of different functional stages of the first activator embodiment comprised in a medicament delivery device of FIG. 1.

The relative movement of the housing parts will further cause the distal end surface of the proximal housing part 18 to come in contact with the proximally directed ledge 152 of the actuator sleeve 146, wherein the latter is also moved in the distal direction. The movement of the actuator sleeve 146 will in turn cause a distal end of the actuator sleeve 146 to come in contact with the tongues 62 of the rear distal housing part 24 and bias the hooks 65 outwards in the generally radial direction, FIG. 10. The engagement surfaces 67 of the ledges 64 will then move out of contact with the stop surfaces 83 of the beams 82 of the activator sleeve 74. Further, the proximal end surface of the actuator sleeve 146 has now moved in relation to the outwardly directed ledges 138 of the arms 134 of the actuator 124, as seen in FIG. 10, such that the end surface of the actuator sleeve 146 is generally in line with the proximal end surface of the actuator 124. When the proximal housing part 18 is in the most retracted position inside the distal housing part, the ledge 38 has entered the second cut-out 4011 of the distal housing part, which locks the proximal housing part from being rotated back.

The medicament delivery device is now ready for delivering a dose of medicament. A medicament delivery member is attached to the proximal end of the proximal housing part 18, wherein a priming of the medicament container 50 may be performed. In order to activate the medicament delivery device, the activator blocker 88 of the activator 90 is pulled in the distal direction, which may be facilitated by the grip elements 96 on the side surface thereof. Due to the connection with the activator sleeve 74, the latter will also be moved distally, wherein the distally directed arms 104 of the activator element 100 will flex radially inwards due to the wedge-shaped ledges 106 coming in contact with the inwardly directed ledges 80 of the activator sleeve 74 until the ledges 80 of the activator sleeve 74 are positioned between the ledges 106 of the arms 104 of the activator element 100, FIG. 11. The activator sleeve 74, and thus the activator blocker 88, is now operably connected in the longitudinal direction with the activator element 100.

Figure 12A:
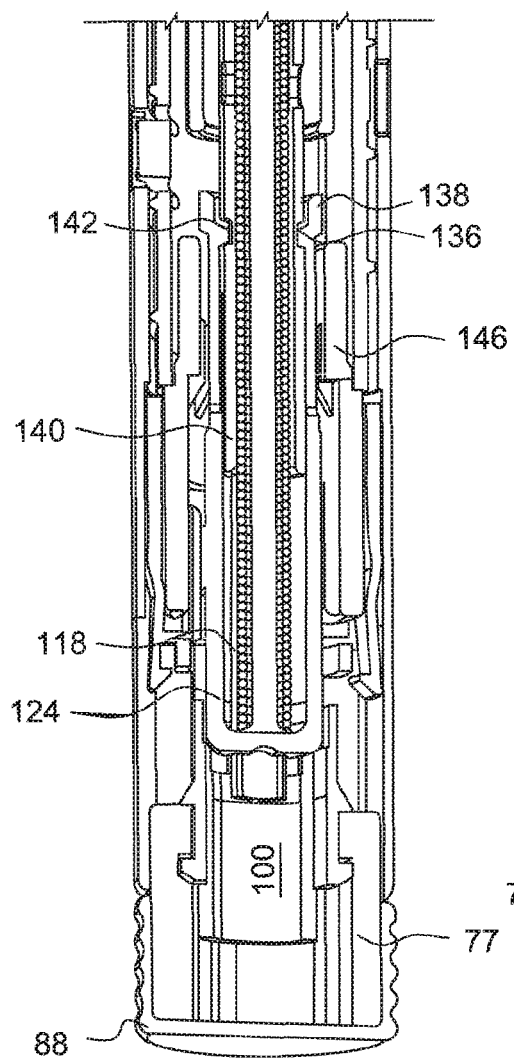
FIG. 12 is a cross-sectional view of different functional stages of the first activator embodiment comprised in a medicament delivery device of FIG. 1.
Figure 12B:
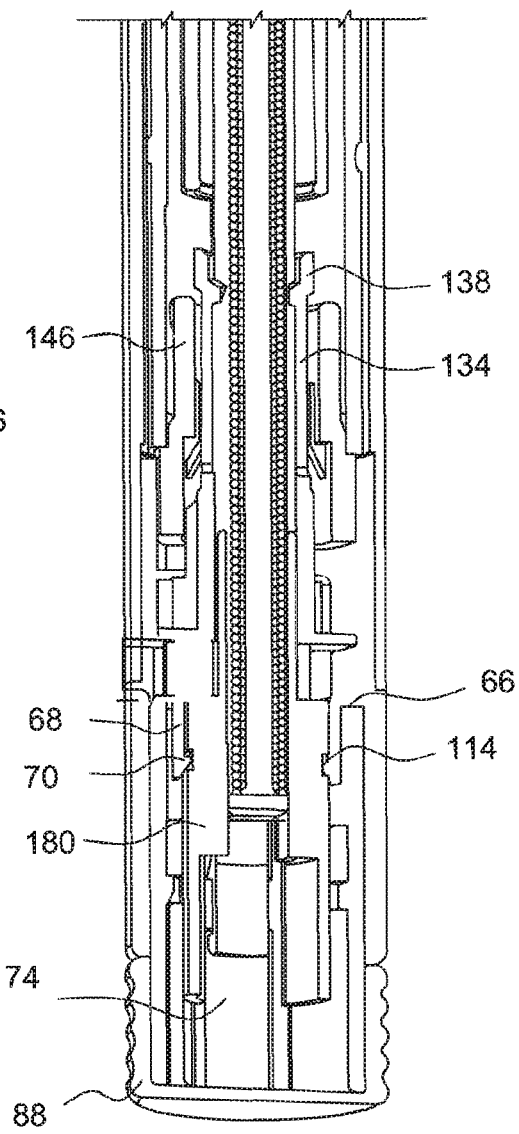

The next step is now to perform a penetration whereby the proximal end with the medicament delivery member is pressed against a dose delivery site. After that the user presses on the distal end wall 98 of the activator blocker 88 whereby the activator 90, i.e. the activator blocker 88, the activator sleeve 74 and the activator element 100 are moved in the proximal direction in relation to the rest of the medicament delivery device. This movement of the activator element 100 will cause its proximally directed fingers 118 to move inside the actuator 124 such that the proximal end surfaces of the fingers come in contact with a distal end surface of the plunger rod 140, FIG. 12a. This in turn will cause the plunger rod 140 also to move in the proximal direction together with the actuator 124 due to the connection of the inwardly directed ledges 136 in engagement with the circumferential groove 142 of the plunger rod 140. Now the movement of the actuator 124 will cause the outwardly directed ledges 138 of the arms 134 to move out of engagement with the actuator sleeve 146, FIG. 12b, whereby the arms 134 are free to flex in the radial direction, releasing the plunger rod 140. In this position, the activator blocker 88 is again in contact with the distal housing part, FIG. 11*b*, stopping further movement of the activator 90. In this position of the activator 90 and thus the activator element 100, the inwardly directed ledges 70 of the protrusions 68 on the transversal wall section 66 of the rear distal housing part 24 to engage the transversal grooves 114 of the activator, thereby locking the activator element 100 in the longitudinal direction, and thereby also the activator sleeve 74 and the activator blocker, FIG. 12*b*.

Figure 13:
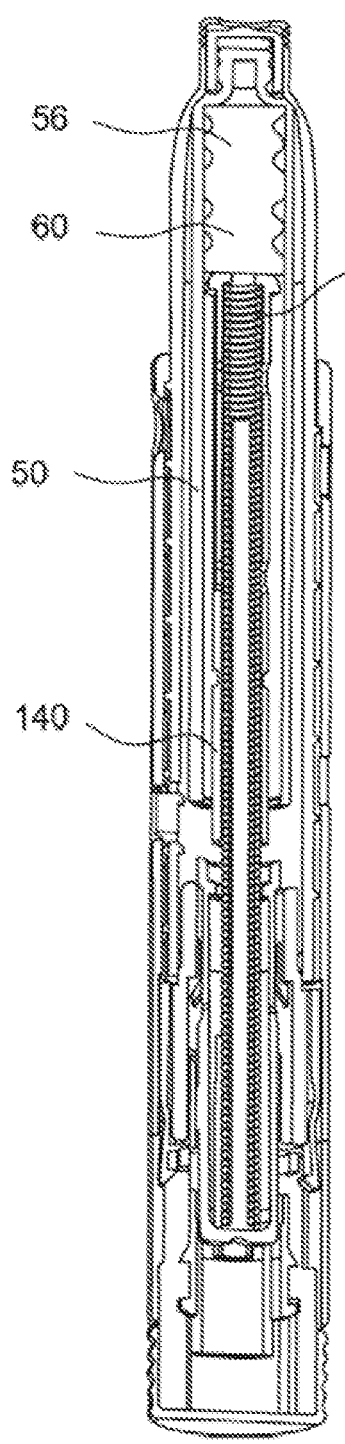
FIG. 13 is a cross-sectional view of different functional stages of the first activator embodiment comprised in a medicament delivery device of FIG. 1.
Figure 14:
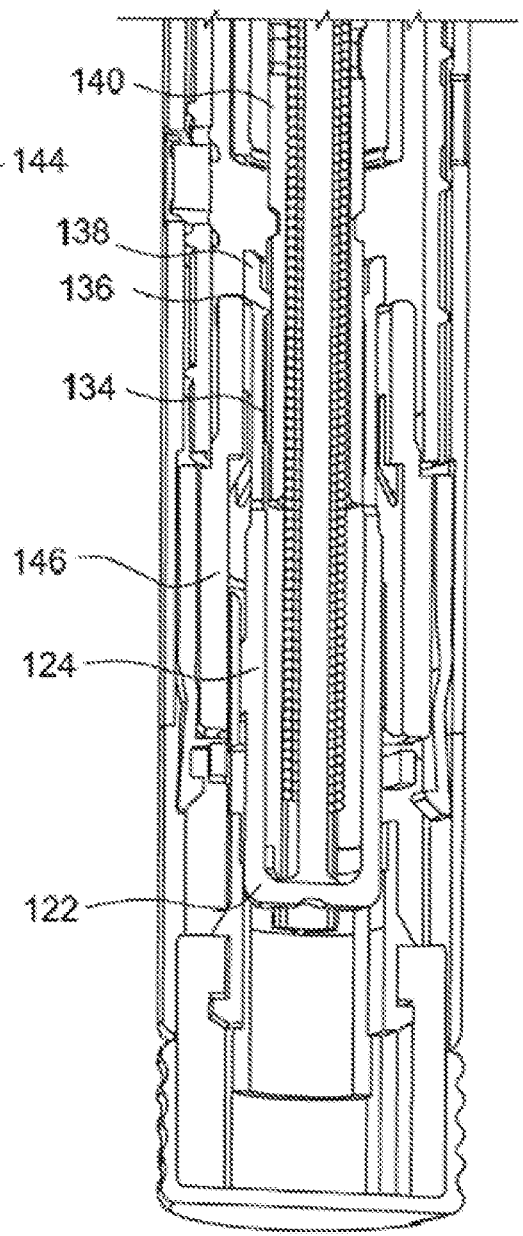
FIG. 14 is a cross-sectional view of different functional stages of the first activator embodiment comprised in a medicament delivery device of FIG. 1.

The now released plunger rod 140 is urged in the proximal direction by the force of the drive spring 144, in turn driving the stoppers 56, 60 in the medicament delivery container 50 in the proximal direction, causing the expelling of a dose of medicament through the medicament delivery member at the dose delivery site, FIG. 13. Further, the release of the arms 134 of the actuator 124 will cause them to be forced suddenly outwards hitting the proximal end surface of the actuator sleeve 146, FIG. 14, causing an audible and tactile signal to the user, informing the user that the dose delivery sequence has started. The actuator 124 is however prevented from being moved in the distal direction by the counter force of the drive spring 144 acting on the end wall 122 of the actuator 124, due to the outwardly directed ledges 138 of the arms 134 engaging the proximal end surface of the actuator sleeve 146 and by the inwardly directed ledges 136 engaging the side surface of the plunger rod 140 as seen in FIG. 14.

Figure 15:
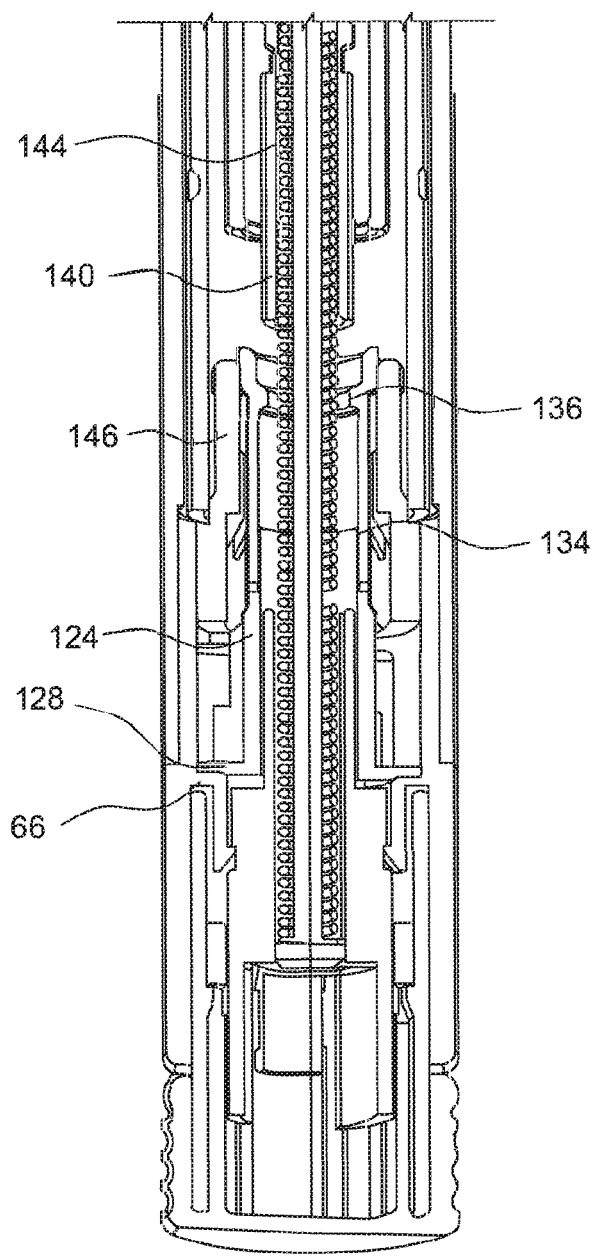
FIG. 15 is a cross-sectional view of different functional stages of the first activator embodiment comprised in a medicament delivery device of FIG. 1.
Figure 16:
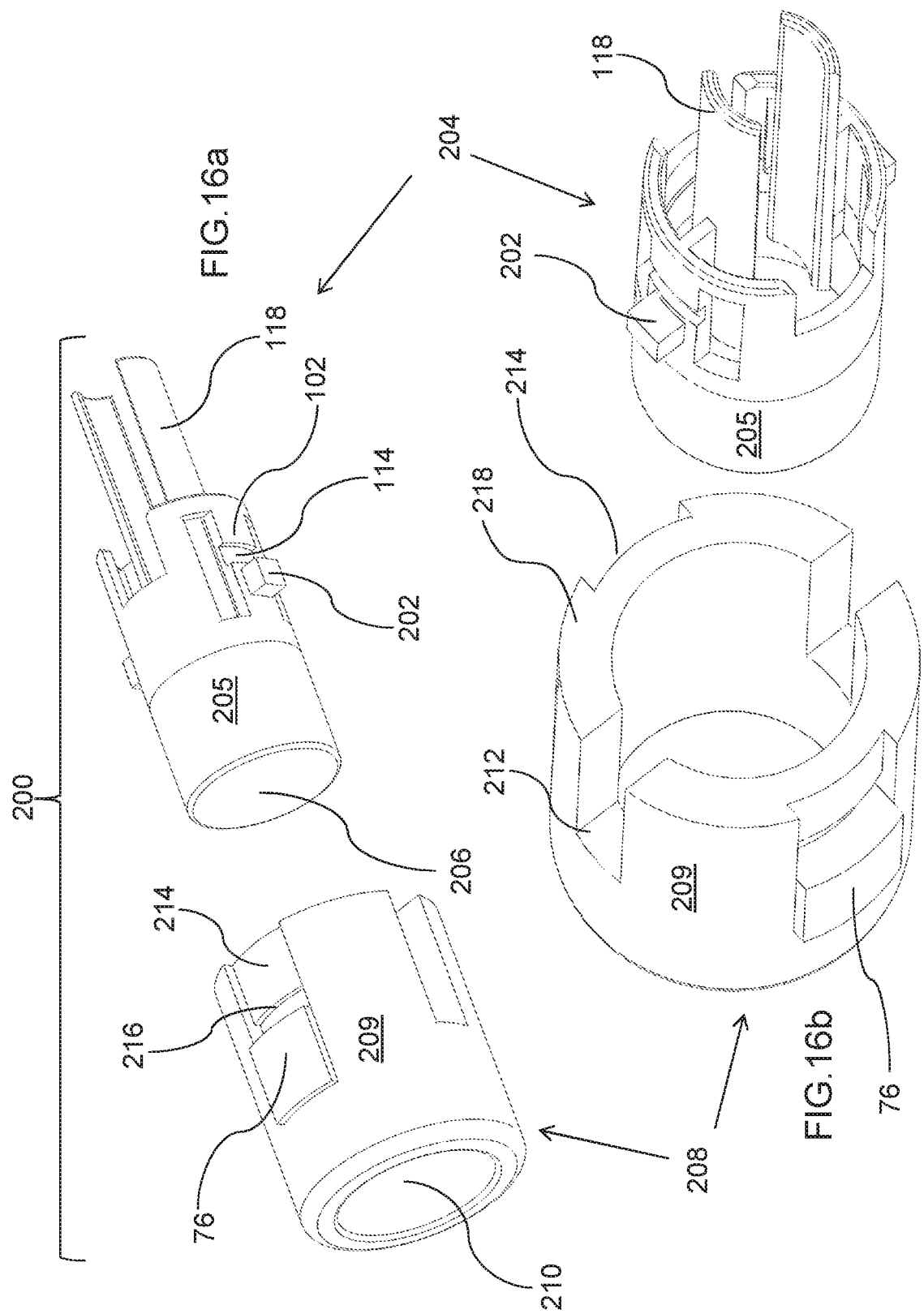
FIG. 16a is a detailed view of components of a second embodiment of an activator of the medicament delivery device of FIG. 1.
FIG. 16b is a detailed view of components of a second embodiment of an activator of the medicament delivery device of FIG. 1.

When the plunger rod 140 has almost come to its most proximal position after dose delivery, its distal end will move out of contact with the inwardly directed ledges 136 of the arms 134 of the actuator 124, FIG. 15. This will cause the actuator 124 to be moved suddenly in the distal direction due to the residual force of the drive spring 144, until the transversal ledges 128 of the actuator 124 hit the proximally directed surfaces of the transversal wall 66 of the distal housing part, FIG. 15, creating a tactile and audible signal, informing the user that the dose delivery sequence has ended. The medicament delivery device can now be safely removed from the dose delivery site and discarded in a safety container for example.

FIGS. 16-21 disclose another embodiment of a medicament delivery device provided with locking features. In this embodiment, only two components are different from the previous embodiment, and thus, the components that are the same have retained their reference numerals. One of the components or elements that is different is an activator 200, where the difference is that there are generally rectangular protrusions 202 on the side surface forming the bridge 112 and distal of the transversal groove 114 of an activator element 204. The activator element 204 of the activator 200 of the second embodiment comprises a distal tubular section 205 and a distal end wall 206, which will function as a contact surface as will be described. For the rest, the activator is arranged with proximally directed fingers 118 as the previous embodiment. The distal section 205 of the activator element 204 is intended to fit into an activator blocker 208 having a generally tubular body 209 with an inner diameter somewhat larger than the distal section of the activator element 204. The activator blocker 208 is arranged with a distal passage 210 through which the distal end wall 206 of the activator element 204 is visible.

Figure 17:
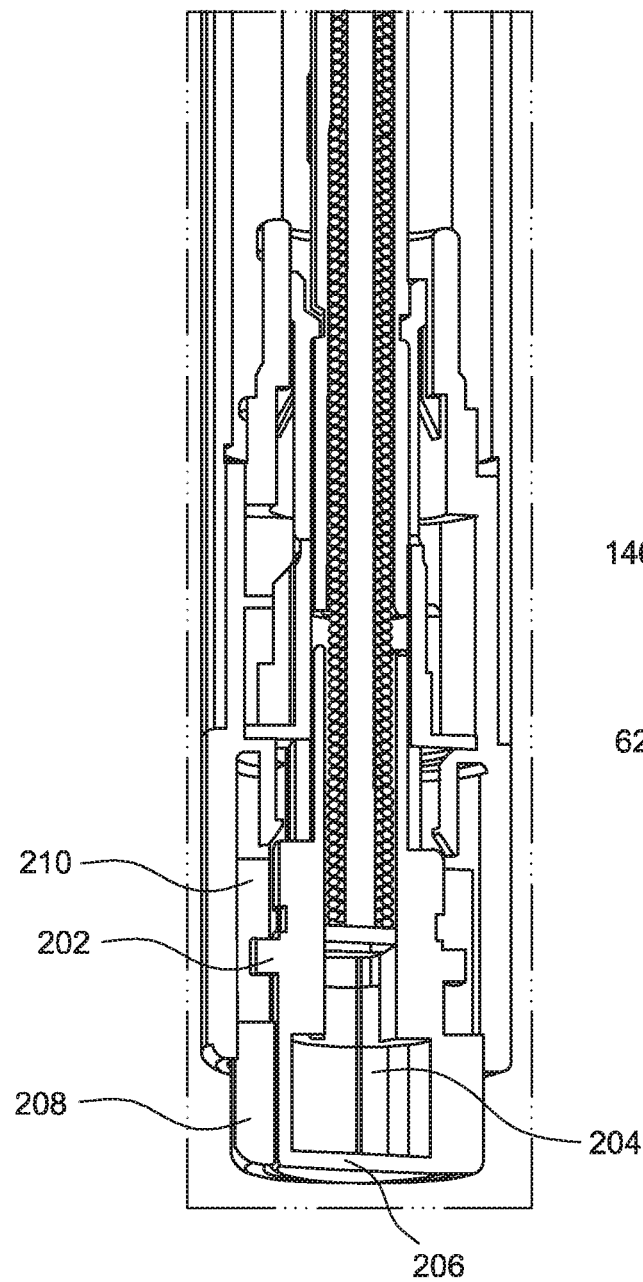
FIG. 17 is a cross-sectional view of different functional stages of the second activator embodiment comprised in a medicament delivery device of FIG. 1.

The activator blocker 208 is further arranged with longitudinally extending grooves 212 running from the distal end surface, in which grooves 212 the rectangular protrusions 202 of the activator element 204 are designed to fit. The design of the activator blocker 208 and the activator element 204 are formed such that the distal end wall 206 of the activator element 204 is generally in level with the distal end surface of the activator blocker 208 as seen in FIG. 17. The activator blocker 208 is further arranged with longitudinally extending ledges 76 that are intended to fit into the grooves 72 of the distal housing part. Moreover, proximally of the ledges 76, grooves 214 are arranged, which grooves 214 are provided with transversal ledges 216. These ledges 216 are designed to interact with the ledges 64 of the hooks 65 of the rear distal housing part 24. Further, a proximally directed end surface 218 of the activator blocker 208 functions as stop surface as will be described.

Figure 18:
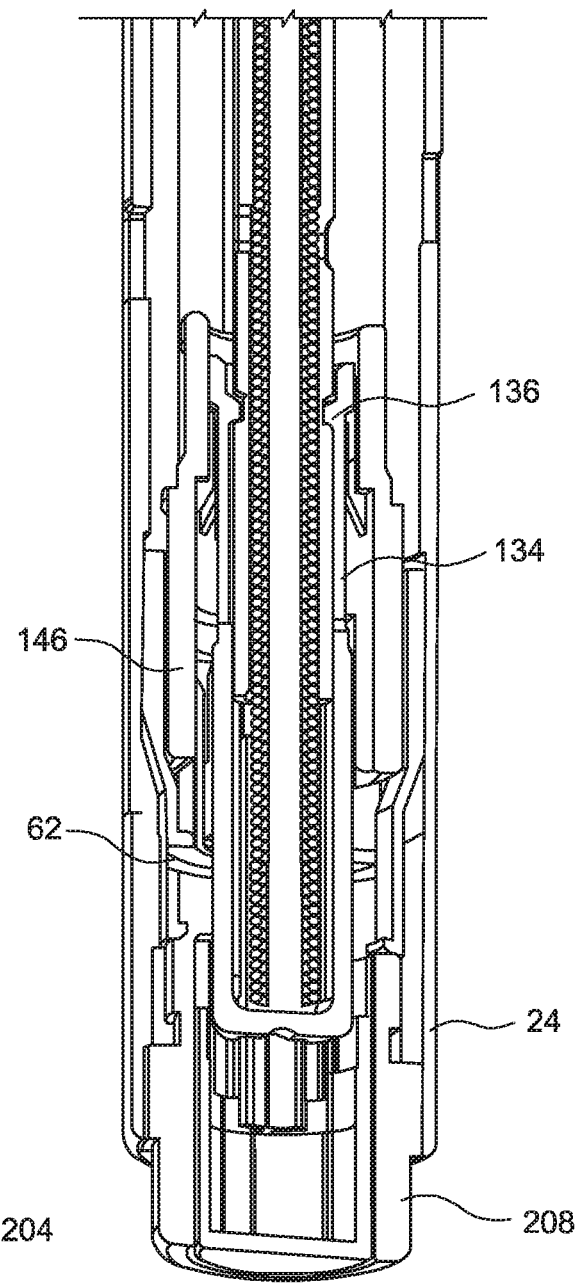
FIG. 18 is a cross-sectional view of different functional stages of the second activator embodiment comprised in a medicament delivery device of FIG. 1.
Figure 19:
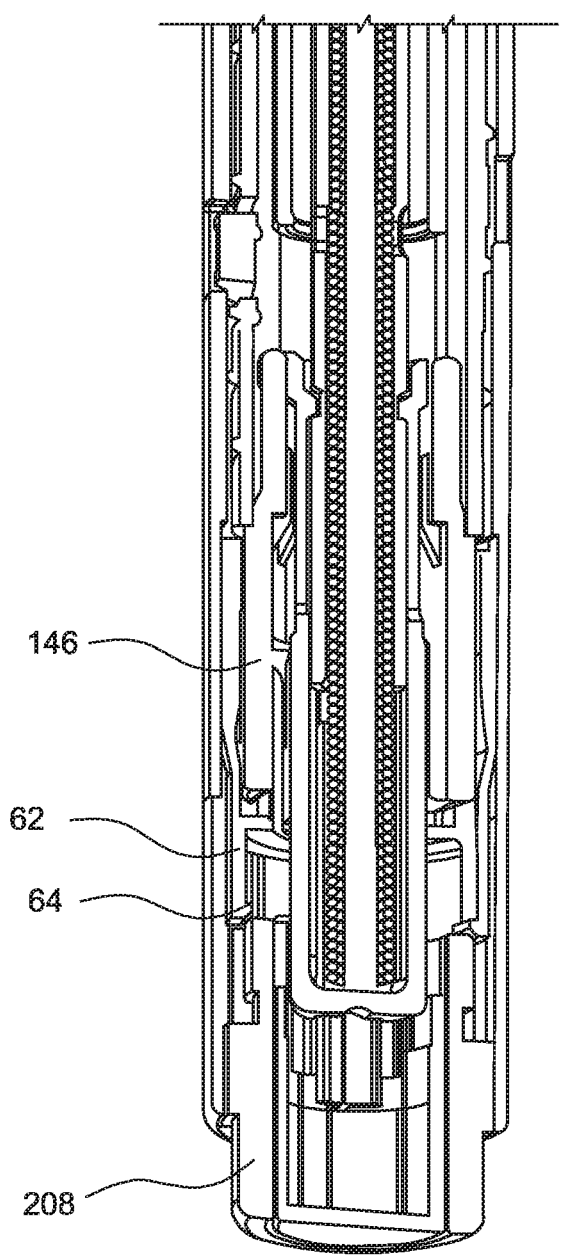
FIG. 19 is a cross-sectional view of different functional stages of the second activator embodiment comprised in a medicament delivery device of FIG. 1.
Figures 20, 21:
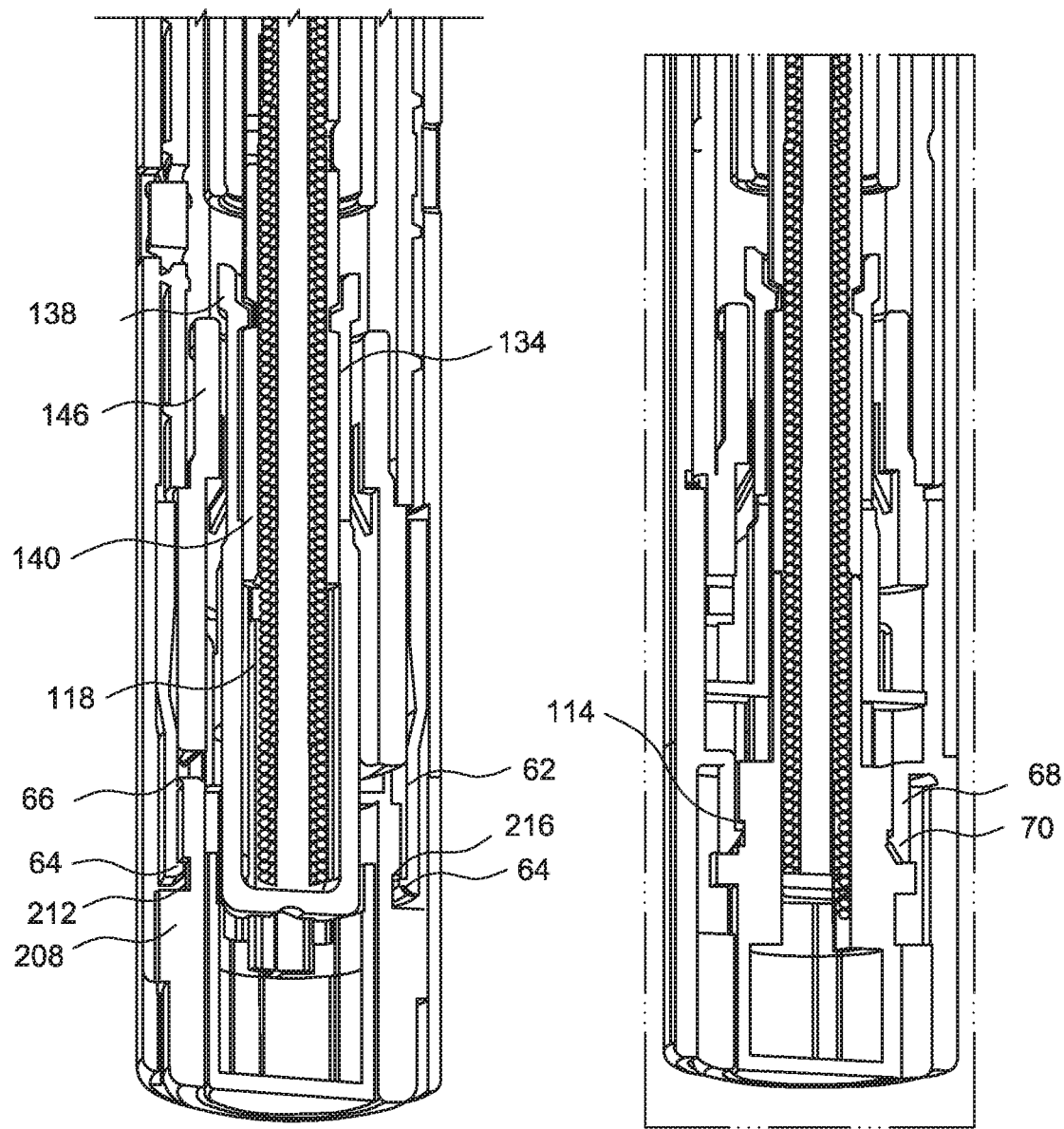
FIG. 20 is a cross-sectional view of different functional stages of the second activator embodiment comprised in a medicament delivery device of FIG. 1.
FIG. 21 is a cross-sectional view of different functional stages of the second activator embodiment comprised in a medicament delivery device of FIG. 1.
Figure 22:
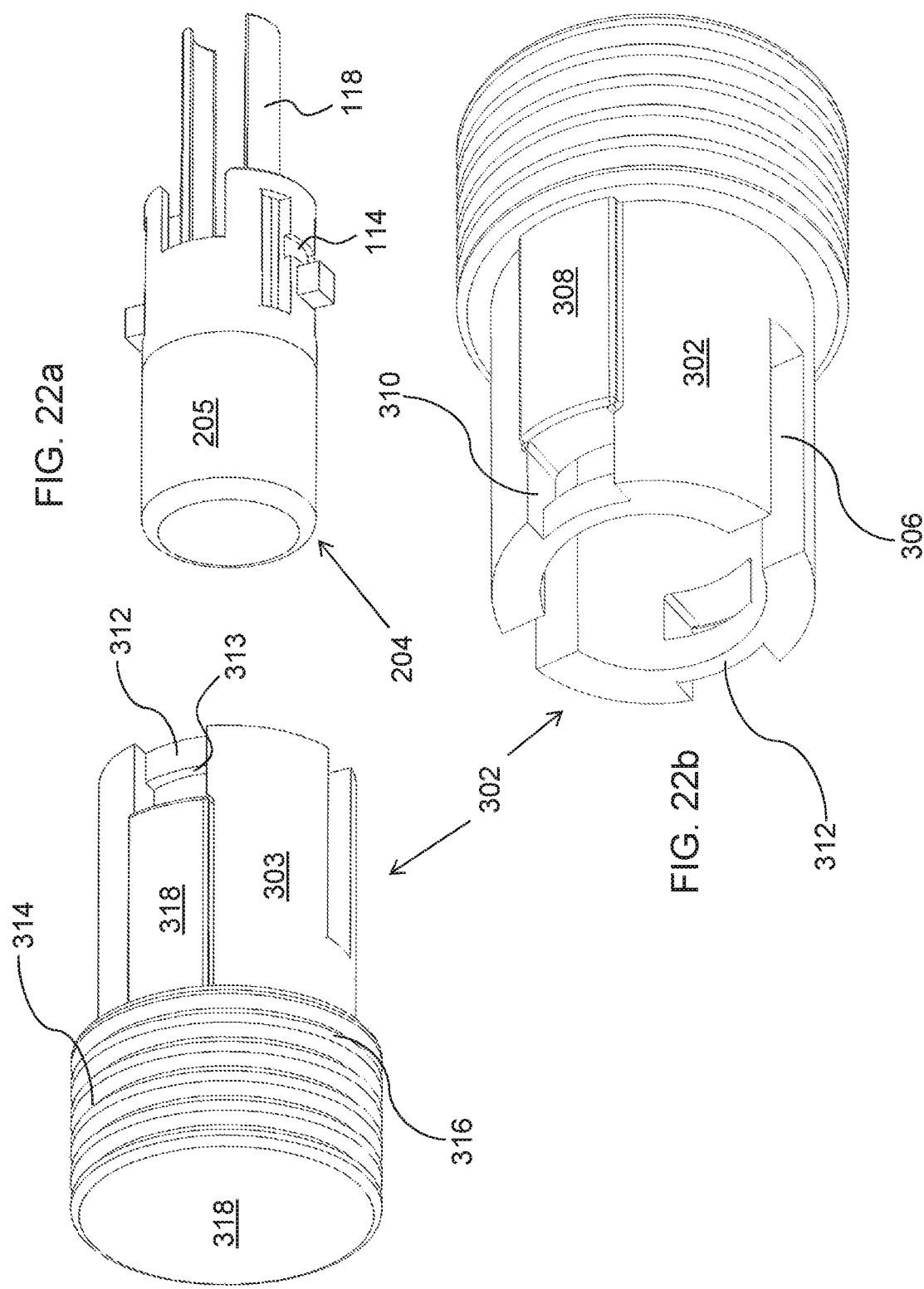
FIG. 22a is a detailed view of components of a third embodiment of an activator of the medicament delivery device of FIG. 1.
FIG. 22b is a detailed view of components of a third embodiment of an activator of the medicament delivery device of FIG. 1.

The medicament delivery device according to the second embodiment is intended to function as follows. As with the previous embodiment the proximal housing part 18 is in an extended position in relation to the rear distal housing part 24 when delivered to a user. The plunger rod 140 is held in a tensioned state by the inwardly ledges 136 of the arms 134 of the actuator 124, wherein the arms 134 are held in position by the actuator sleeve 146. The activator element 204 cannot be operated since the surrounding activator blocker 208 is locked from movement in the longitudinal direction because the proximally directed stop surface 218 of the activator blocker 208 is in engagement with distally directed engagement surfaces 220, FIG. 5*a*, of the ledges 64 of the hooks 65 as seen in FIG. 18. The user now performs a mixing action by rotating the proximal housing part in relation to the distal housing part, whereby the plunger rod will act on the stoppers 56, 60 of the medicament container 50 as described above. The proximal housing part 18 will as described come in contact with the proximally directed end surface of the actuator sleeve 146, which will then move the actuator sleeve 146 in the distal direction in relation to the actuator 124. Also the distal end surface of the actuator sleeve will come in contact with and bias the tongues 62 of the hooks 65 outwardly in the radial direction as seen in FIG. 19.

When now the mixing has been performed and the medicament delivery device is placed at the dose delivery site, the user can press on the distal end wall 206 of the activator element 204 whereby it will move in the proximal direction together with the activator blocker 208. Since the hooks 65 have been moved radially outwardly, the proximal edge surface of the activator blocker 208, which may be somewhat beveled, comes in contact with the inclined surface of the ledge 64, forcing the hook 65 to be biased further outwardly in the radial direction. The hooks 65 will then slide along the outer side surface of the activator blocker 208. As with the previous embodiment, the movement in the proximal direction of the activator element 204 will cause its fingers 118 to contact and move the plunger rod 140 and the actuator 124 in the proximal direction until the outwardly ledges 138 of the arms 134 of the actuator 124 are moved out of contact with the actuator sleeve 146, FIG. 20, whereby the plunger rod 140 is released and performs a dose delivery operation as described above.

When the activator element 204 and the activator blocker 208 have been pressed in the proximal direction until the activator blocker 208 abuts the transversal wall section 66 of the rear distal housing part 24, the activator blocker 208 is locked in that the ledges 64 of the hooks 65 engage with the transversal ledges 216 of the activator blocker 208. Further the ledges 70 of the protrusions 68 of the rear distal housing part 24 enter the transversal grooves 114 of the activator 200, FIG. 21. The activation mechanism is thus locked in the depressed position, indicating that the medicament delivery device has been used. The signaling functions described in the previous embodiment are also present in the second embodiment.

FIGS. 22-25 disclose a third embodiment. It comprises an activator 300 comprising an activator blocker 302 provided with a generally tubular body 303 having an inner diameter generally corresponding to the outer diameter of an activator element 304, which activator element 304 generally has the same shape as the activator element of the second embodiment, having a body 305 and being provided with rectangular protrusions 307. The body 303 of the activator blocker 302 is arranged with longitudinally extending grooves 306, in which the rectangular protrusions 307 of the activator element 304 fit. The activator blocker 302 is further arranged with generally rectangular protrusions 308 on its outer surface, which protrusions fit into the longitudinal grooves 72 of the inner surface of the rear distal housing part 24. Proximal of the rectangular protrusions 308 are generally rectangular cut-outs 310, wherein the proximal area of the cut-outs are provided with transversal beams 312. The transversal beams 312 are arranged with distally directed stop surfaces 313 that are arrange to interact with the proximally directed engagement surfaces 67 of the hooks 65. The distal end of the activator blocker 302 is provided with a grip part 314 having a diameter generally as large as the diameter of the distal housing part. The grip part 314 may be arranged with grip enhancing elements such as circumferential grooves and protrusions 316. The grip part 314 is further arranged with an end wall 318.

Figure 23:
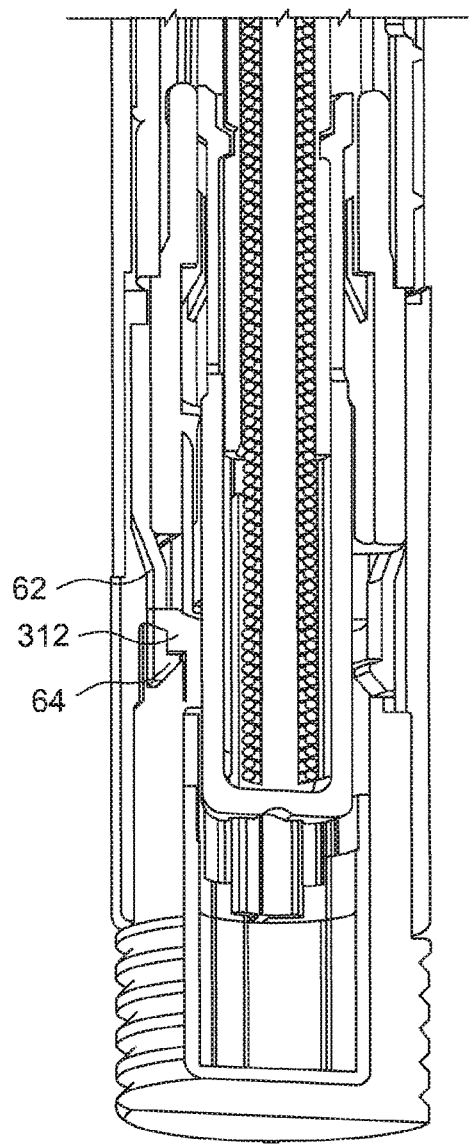
FIG. 23 is a cross-sectional view of different functional stages of the third activator embodiment comprised in a medicament delivery device of FIG. 1.
Figure 24:
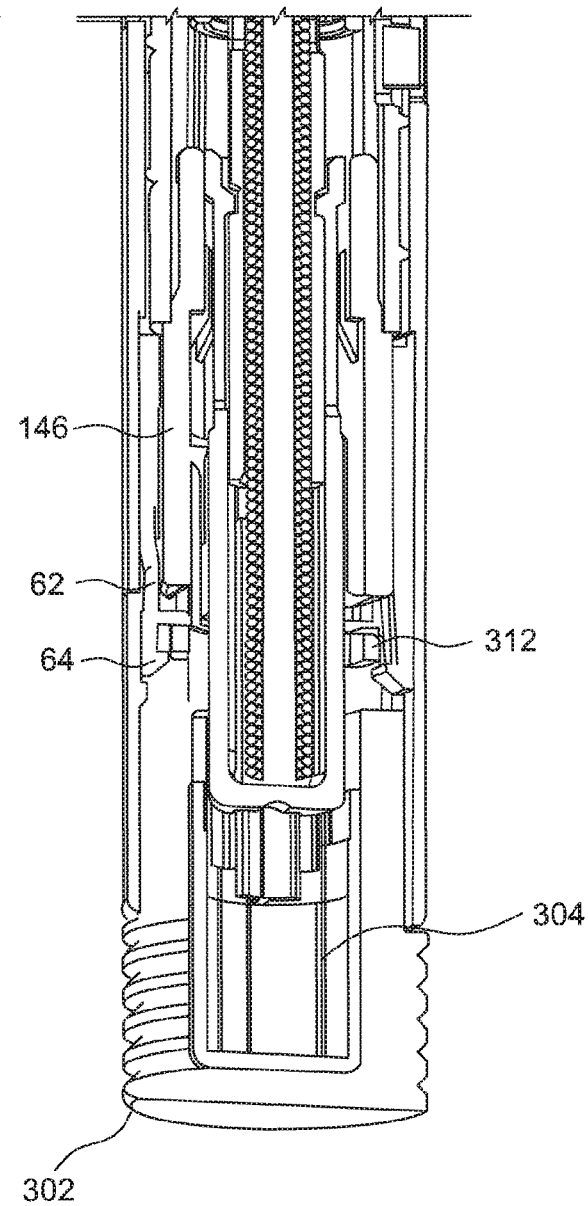
FIG. 24 is a cross-sectional view of different functional stages of the third activator embodiment comprised in a medicament delivery device of FIG. 1.
Figure 25:
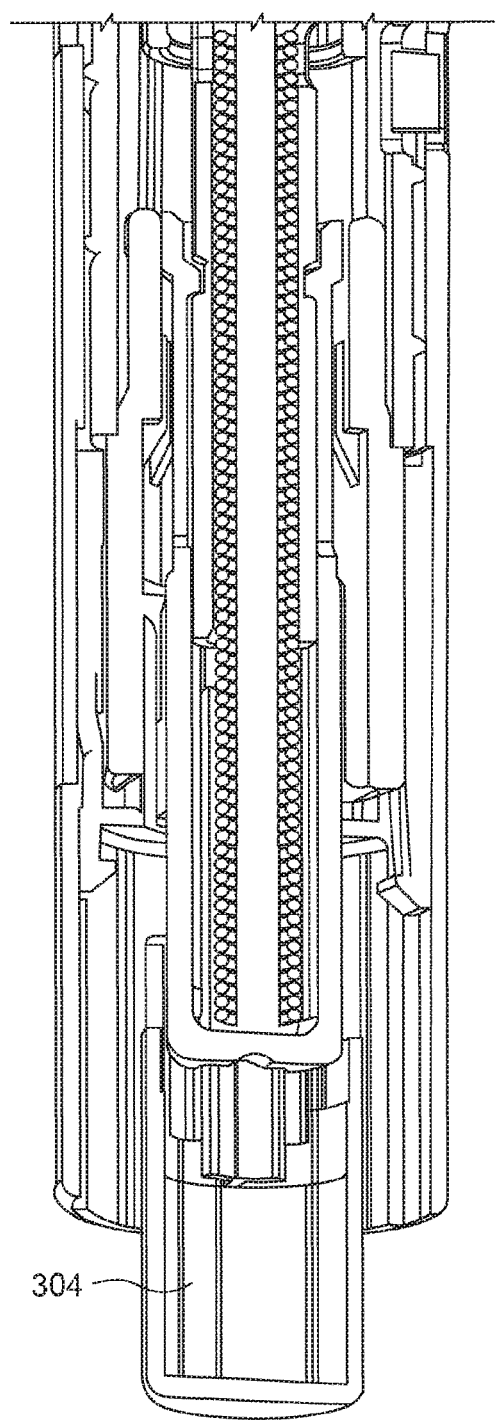
FIG. 25 is a cross-sectional view of different functional stages of the third activator embodiment comprised in a medicament delivery device of FIG. 1.
Figure 28A:
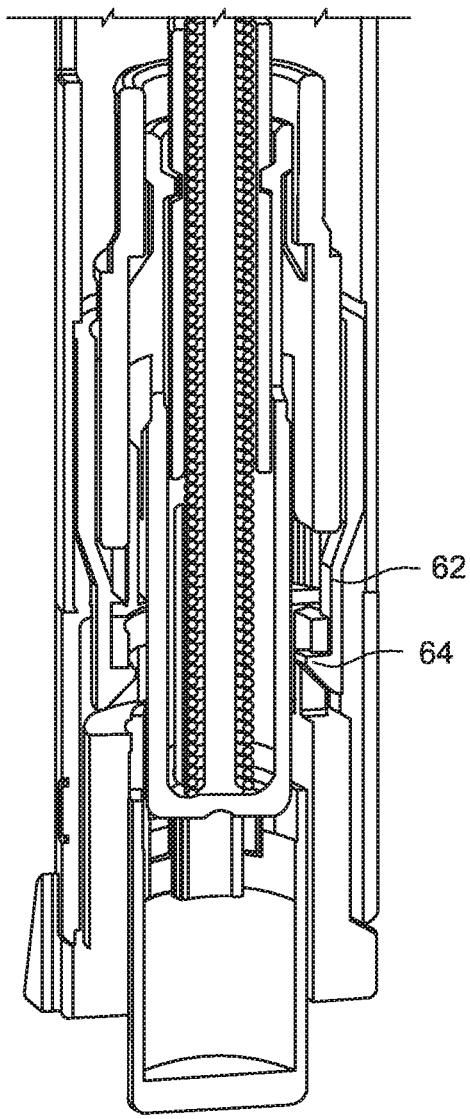
FIG. 28a is a cross-sectional view of a first and a second functional stage respectively of the fourth activator embodiment comprised in a medicament delivery device of FIG. 26.
Figure 28B:
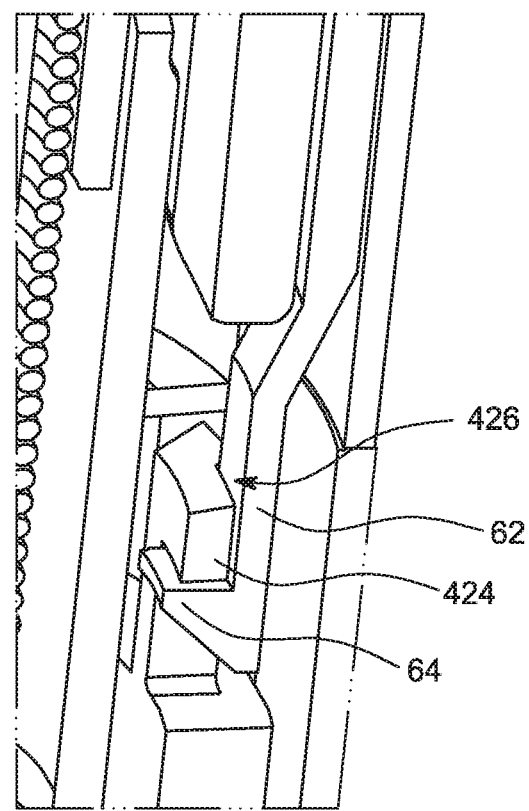
FIG. 28b is a cross-sectional view of a first and a second functional stage respectively of the fourth activator embodiment comprised in a medicament delivery device of FIG. 26
Figure 30A:
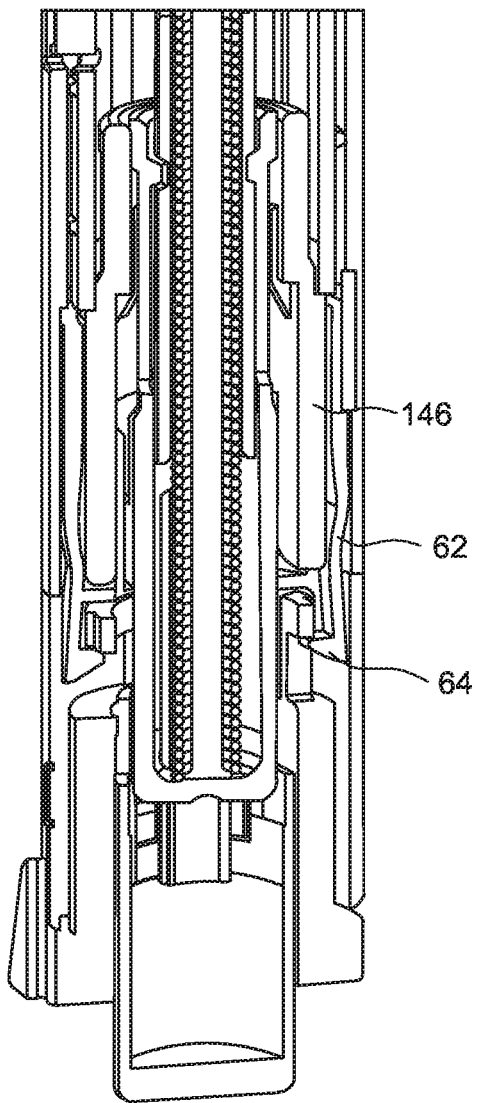
FIG. 30a is a cross-sectional view of a first and a second functional stage respectively of the fourth activator embodiment comprised in a medicament delivery device of FIG. 26
Figure 30B:
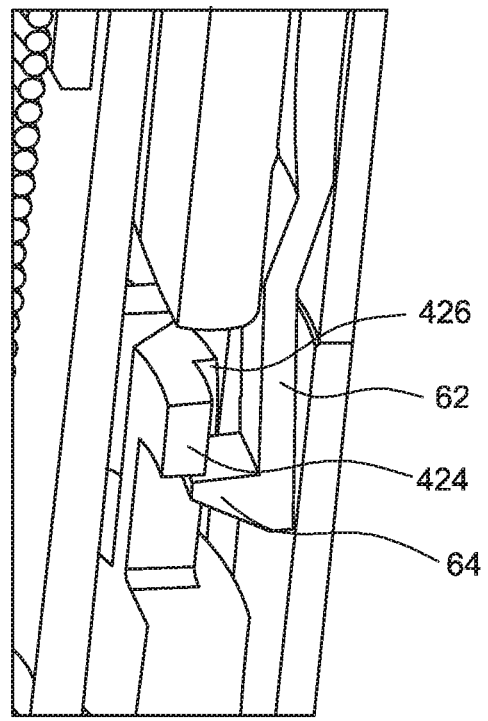
FIG. 30b is a cross-sectional view of a first and a second functional stage respectively of the fourth activator embodiment comprised in a medicament delivery device of FIG. 26

When the medicament delivery device is delivered to a user, the activator blocker 302 is inserted into the distal end of the medicament delivery device. The engagement surfaces 67 of the ledges 64 of the hooks 65 of the rear distal housing part 24 are engaging the stop surfaces 313 of the transversal beams 312 of the activator blocker 302 as seen in FIG. 23, preventing any removal of the activator blocker 302. When the mixing of the medicament delivery device is performed as described earlier, the distal end of the moving actuator sleeve 146 will contact the tongues 62 of the hooks 65 and bias them in the radial direction, whereby the ledges 64 of the hooks 65 are moved out of engagement with the transversal beams 312, FIG. 24. The activator blocker 302 is thus released and can be pulled in the distal direction away from the medicament delivery device. The distal part of the activator element 304 is now exposed, FIG. 25, and can be pushed in the proximal direction for delivering a dose of medicament in the same manner as described above.

FIGS. 26-32 shows a fourth embodiment. An activator 400 is arranged at the distal end of the medicament delivery device. The activator 400 is arranged with an activator blocker 402 provided rotatable in relation to the distal housing part. The activator blocker 402 is provided with a generally tubular body 403 having an outer diameter generally corresponding to the inner diameter of the distal housing part. At the distal end of the body 403 a generally ring-shaped grip part 404 is provided having a diameter generally corresponding to the outer diameter of the distal housing part. An indicator 406 is attached to or made integral with the grip part 404, extending in the longitudinal direction proximally. The indicator 406 is arranged to point at different indicia 408 on the outer surface of the housing, wherein the indicia 408 may be numbers like "0" and "1" or symbols like a locked padlock or unlocked padlock.

The body 403 of the activator blocker 402 is further arranged with circumferentially extending groove sections 410, FIG. 27. These groove sections 410 connect with longitudinally extending groove sections 412 that end at the proximal end surface of the body 402. These groove sections 410, 412 are arranged to interact with rectangular protrusions 414 on the outer surface of an activator element 416. The activator element 416 of the fourth embodiment is similar to the activator element of the second embodiment. However, the rectangular protrusions 414 of the fourth embodiment are placed on the side of rectangular cut-outs 418 instead of on a bridge 420.

At the proximal end surface of the body 403 of the activator blocker 402, generally rectangular, arc-shaped sections 422 are attached or made integral. The transversal part 424 of each arc-shaped section 422 is provided with an outwardly directed cut-out 426 provided with side surfaces 428 that will function as stop surfaces as will be described.

When the medicament delivery device is delivered to a user, the proximal housing part is extended in relation to the distal housing part as described above. The activator blocker 402 is positioned with its indicator 406 towards the initial indicia, such as zero, as shown in FIG. 26. The activator blocker 402 is locked in this rotational position by the tongues 62 of the hooks 65 fitting into the outwardly directed cut-outs 426 of the arches, whereby side surfaces 430 of the tongues 62 of the hooks 65 are engagement surfaces that are in blocking contact with the stop surfaces 428 of the cut-outs 426, FIG. 28. The activator blocker 402 is further locked in the distal direction by the ledges 64 of the hooks 65 of the rear distal housing part 24 engaging distally directed surfaces of the transversal parts 424 of the arc-shaped sections 422. Further, in the initial position the protrusions 414 of the activator 416 are positioned at one end of the circumferential groove section 410 of the body 403 of the activator blocker 402, FIG. 29. The distal end of the activator element 416 protrudes out of the activator blocker 402 but is prevented from being depressed by the protrusions 414 positioned in the transversal groove sections 410.

Figure 31:
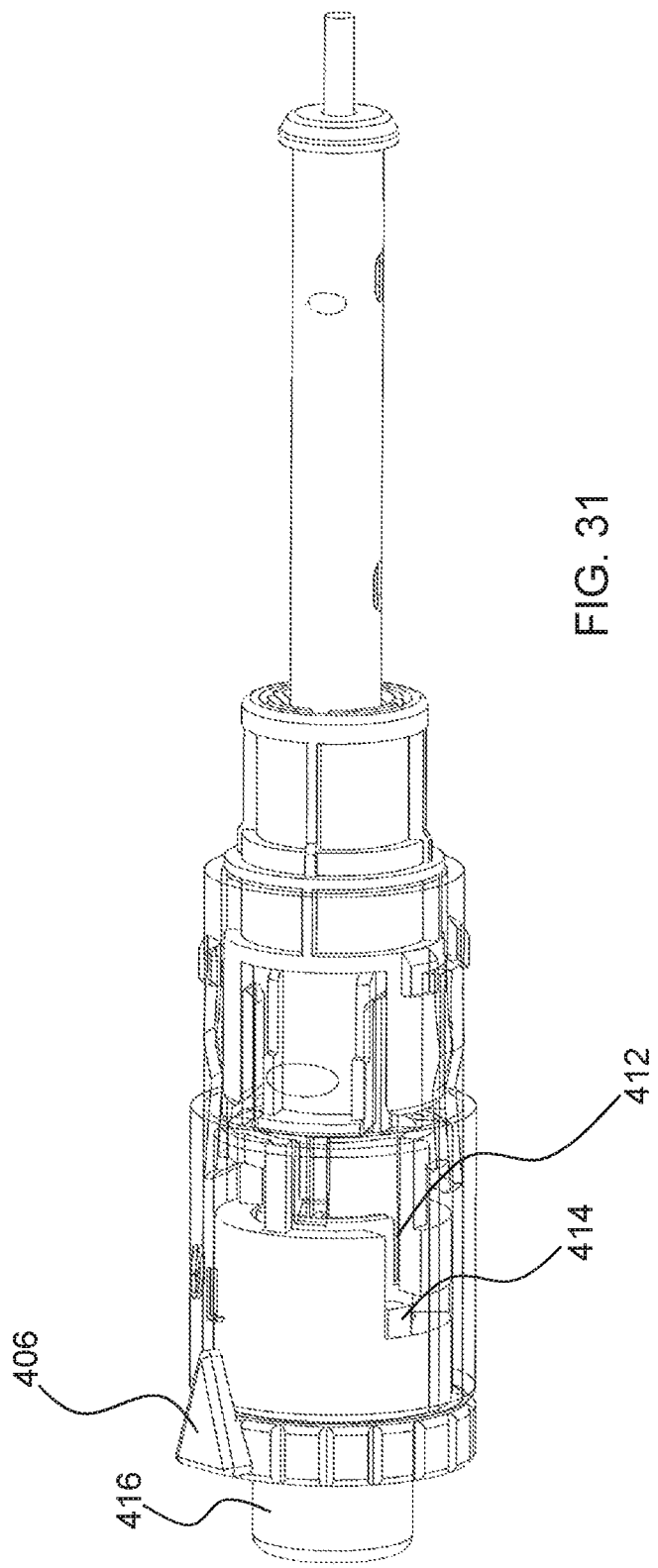
FIG. 31 is a side view of the medicament delivery device of FIG. 26 with certain components removed for clarity, displaying different functional stages.

When now a mixing operation is performed, the distal end of the proximal housing part 18 engages the actuator sleeve 146 and pushes it in the distal direction. The distal end of the actuator sleeve 146 is then moved in contact with the tongues 62 of the hooks 65, biasing the hooks 65 outwards in the radial direction, FIG. 30. This will cause the engagement surfaces 430 of the hooks 65 to be moved out of contact with the stop surfaces 428 of the cut-outs 426 of the arc-shaped sections 422, FIG. 30b. However, the hooks 65 are biased such that the ledges 64 still engage the arc-shaped sections 422, FIG. 30b, still locking the activator blocker 402 in the longitudinal direction. Since the activator blocker 402 now is free to rotate, a user may turn the activator blocker 402 so that the indicator 406 is pointing to the unlocked indicia such as "1" as seen in FIG. 31. This has caused the protrusions 414 to move in the transversal groove sections 410 to the point where these grooves meet the longitudinal groove sections 412, FIG. 31. This enables the activator element 416 to be pushed or pressed in the proximal direction and when the medicament delivery device has been placed at a dose delivery site, the activator element 416 is pushed in the proximal direction, FIG. 32. This causes a release of the tensioned plunger rod 140 and a dose delivery sequence is performed as described earlier.

It is to be understood that the embodiments described above and shown in the drawings are to be regarded only as a non-limiting example of the disclosure and that they may be modified in many ways within the scope of the patent claims. It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

The invention claimed is:

1. An activator for a medicament delivery device, comprising:
a manually operable activator element;
an activator blocker operably arranged to said manually operable activator element, said activator blocker defining at least one locking member; and
a medicament delivery device housing comprising at least one flexible hook, wherein the at least one flexible hook of the medicament delivery device housing is operably between a locked position and an unlocked position, where in the locked position the at least one flexible hook is releasably engaged with the at least one locking member of the activator blocker to prevent operation of said manually operable activator element and where in the unlocked position the at least one flexible hook is out of engagement with the at least one locking member of the activator blocker to allow operation of said manually operable activator element, and wherein said at least one flexible hook is arranged to engage with a locking structure of said manually operable activator element for locking said manually operable activator element in an active position after manual operation.

2. The activator according to claim 1, wherein said at least one flexible hook is arranged with engagement surfaces arranged to engage with stop surfaces of said activator blocker when in the locked position.

3. The activator according to claim 2, wherein said engagement surfaces of said at least one flexible hook are directed in a proximal direction and wherein said stop surfaces of said activator blocker are directed in a distal direction, preventing movement of said activator blocker in the distal direction in the locked position.

4. The activator according to claim 3, wherein said activator blocker comprises a blocking element enclosing said manually operable activator element, that said activator blocker and said manually operable activator element comprise connection elements and wherein said activator blocker is movable in the distal direction in relation to said manually operable activator element when in said unlocked position such that said connection elements engage the activator blocker with the manually operable activator element, enabling a manual movement in the proximal direction of the activator.

5. The activator according to claim 4, wherein said connection elements comprise flexible arms on said manually operable activator element having ledges that are intended to engage with ledges of said activator blocker.

6. The activator according to claim 2, wherein said activator blocker comprises a blocking element enclosing said manually operable activator element, wherein said activator blocker is movable in a distal direction in the unlocked position, thereby removing said activator blocker and exposing said manually operable activator element, enabling movement of said activator in a proximal direction.

7. The activator according to claim 2, wherein said engagement surfaces of said at least one flexible hook are directed in a distal direction and wherein said stop surfaces of said activator blocker are directed in a proximal direction, preventing movement of said activator blocker in the proximal direction in the locked position.

8. The activator according to claim 2, wherein said engagement surfaces of said at least one flexible hook are directed in a circumferential direction and wherein said stop surfaces of said activator blocker are directed in a circumferential, opposite, direction, preventing movement of said activator blocker in a proximal direction in the locked position.

9. The activator according to claim 8, wherein said activator blocker comprises a generally tubular member arranged turnable in relation to said medicament delivery device housing between an initial position and an activated position, that said manually operable activator element is arranged coaxial inside said activator blocker and protruding in a distal direction, that said activator blocker and said manually operable activator element are provided with engagement elements that in the initial position engage such to prevent movement of said manually operable activator element in the proximal direction and in the activated position are moved out of engagement, allowing movement of the manually operable activator element in the proximal direction.

10. The activator according to claim 9, wherein the engagement elements of said manually operable activator element comprises protrusions, and the engagement elements of said activator blocker comprise a first transversally extending groove and a proximally extending groove.

11. The activator according to claim 1, wherein said activator blocker comprises a blocking element enclosing said manually operable activator element, wherein said activator blocker is movable in a proximal direction in the unlocked position, also enabling movement of said manually operable activator element in the proximal direction.

12. An activator for a medicament delivery device, comprising:
a manually operable activator element;
an activator blocker operably arranged to said manually operable activator element;
a radial flexible member arranged to be fixed on an inner surface of a housing of the medicament delivery device, wherein the radial flexible member is operably between a locked position where the radial flexible member is releasably engaged with the activator blocker, such that a movement of the activator blocker in relation to the housing is prevented and thereby preventing operation of said manually operable activator element; and an unlocked position where the radial flexible member is out of engagement with the activator blocker, thereby allowing the movement of the activator blocker in relation to the housing.

13. The activator according to claim 12, wherein said activator blocker is removable in relation to the housing in the unlocked position such that the removal of said activator blocker exposes said manually operable activator element and thereby enabling movement of said activator in a proximal direction.

14. The activator according to claim 12, wherein the activator blocker is turnable in relation to said housing between an initial position and an activated position.

15. The activator according to claim 14, wherein said manually operable activator element is coaxially arranged to said activator blocker and protruding in a distal direction of the housing, that said activator blocker and said manually operable activator element are provided with engagement elements that in the initial position engage such to prevent movement of said manually operable activator element in a proximal direction in relation to the housing and in the activated position are moved out of engagement, allowing movement of the manually operable activator element in the proximal direction.

16. A medicament delivery device having a housing comprising a proximal housing part and a distal housing part, said proximal housing part being arranged to accommodate a multi chamber medicament container, wherein the housing parts are arranged movable in relation to each other from an initial position to a mixed position in which the contents of the multi chamber medicament container is mixed, a drive unit arranged to act on said multi chamber medicament container for expelling a of medicament;
- an activator operably connected to said drive unit and arranged with a manually operable activator element wherein the activator is manually operable in a proximal direction between an inactive position and an active position in which said drive unit is activated;
- an activator blocker operably arranged to said manually operable activator element, said activator blocker defining at least one locking member;
- said distal housing part comprising at least one flexible hook, wherein the at least one flexible hook of the distal housing part is operably arranged between a locked position where the at least one flexible hook is releasably engaged with the at least one locking member of the activator blocker, thereby preventing operation of said manually operable activator element; and an unlocked position where the at least one flexible hook is out of engagement with the at least one locking member of the activator blocker, thereby allowing operation of said manually operable activator element, wherein in said mixed position said proximal housing part acts on said flexible hook to move it to said unlocked position, and wherein said at least one flexible hook is arranged to engage with a locking structure of said activator for locking said m activator element in the active position after manual operation.

17. The medicament delivery device according to claim 16, further comprising an actuator sleeve operably connected to said proximal housing part so as to move in conjunction with said proximal housing part and to act on said at least one flexible hook, which said actuator sleeve cooperates with an actuator of said drive unit for holding a plunger rod in an energized state.

18. The medicament delivery device according to claim 17, wherein said actuator is generally tubular, accommodating said plunger rod, that the actuator comprises arms that are flexible in a generally transversal direction, that the free ends of the arms are arranged with radially inwardly directed ledges that fit into recesses of said plunger rod.

19. The medicament delivery device according to claim 18, wherein said activator is arranged with proximally directed fingers extending into said actuator and being in contact with a distal end of the plunger rod.

* * * * *